US011278602B2

(12) United States Patent
Väänänen et al.

(10) Patent No.: US 11,278,602 B2
(45) Date of Patent: Mar. 22, 2022

(54) MEDICINE FOR COVID-19 AND TREATMENT

(71) Applicant: Therapeutica Borealis Oy, Helsinki (FI)

(72) Inventors: Kalervo Väänänen, Turku (FI); Lauri Kangas, Lieto (FI); Matti Rihko, Turku (FI)

(73) Assignee: THERAPEUTICA BOREALIS OY, Helsinki (FI)

( * ) Notice: Subject to any disclaimer, the term of this patent is extended or adjusted under 35 U.S.C. 154(b) by 0 days.

(21) Appl. No.: 17/208,827

(22) Filed: Mar. 22, 2021

(65) Prior Publication Data

US 2021/0299230 A1   Sep. 30, 2021

Related U.S. Application Data

(63) Continuation-in-part of application No. 16/872,108, filed on May 11, 2020, now Pat. No. 11,007,187.

(60) Provisional application No. 63/030,233, filed on May 26, 2020, provisional application No. 63/015,345, filed on Apr. 24, 2020, provisional application No. 62/994,647, filed on Mar. 25, 2020.

(51) Int. Cl.

| | | |
|---|---|---|
| *A61K 38/48* | (2006.01) | |
| *A61K 31/465* | (2006.01) | |
| *A61P 31/14* | (2006.01) | |
| *A61K 31/26* | (2006.01) | |
| *A61K 33/40* | (2006.01) | |
| *A61K 31/7048* | (2006.01) | |
| *A61K 31/216* | (2006.01) | |
| *A61K 31/136* | (2006.01) | |
| *A61K 31/352* | (2006.01) | |
| *A61K 31/4706* | (2006.01) | |
| *A61K 45/06* | (2006.01) | |

(52) U.S. Cl.
CPC ........ *A61K 38/4826* (2013.01); *A61K 31/136* (2013.01); *A61K 31/216* (2013.01); *A61K 31/26* (2013.01); *A61K 31/352* (2013.01); *A61K 31/465* (2013.01); *A61K 31/4706* (2013.01); *A61K 31/7048* (2013.01); *A61K 33/40* (2013.01); *A61K 45/06* (2013.01); *A61P 31/14* (2018.01)

(58) Field of Classification Search
CPC .... A61K 38/4826; A61K 33/40; A61K 31/14; A61K 31/4706; A61K 31/465; A61K 31/352; A61K 31/136; A61K 45/06; A61K 31/216

See application file for complete search history.

(56) References Cited

U.S. PATENT DOCUMENTS

| | | |
|---|---|---|
| 4,990,537 A | 2/1991 | Okuyama et al. |
| 6,572,858 B1 | 6/2003 | Charous |
| 6,720,001 B2 | 4/2004 | Chen et al. |
| 6,930,125 B2 | 8/2005 | Hunt et al. |
| 7,183,112 B2 | 2/2007 | Charous |
| 7,888,385 B2 | 2/2011 | Hunt et al. |
| 8,263,125 B2 | 9/2012 | Vaya et al. |
| 8,466,193 B2 | 6/2013 | Verner et al. |
| 8,637,469 B2 | 1/2014 | Levitt |
| 8,906,954 B2 | 12/2014 | Verner et al. |
| 9,333,260 B2 * | 5/2016 | Pellico ................... A61K 45/06 |
| 11,007,187 B1 * | 5/2021 | Vaananen .............. A61K 31/14 |
| 2004/0167162 A1 | 8/2004 | Charous |
| 2010/0163020 A1 | 7/2010 | Hyde et al. |
| 2011/0008361 A1 * | 1/2011 | Bragger ................. A61K 38/40 |
| | | 424/157.1 |
| 2014/0311482 A1 | 10/2014 | Levitt, Jr. |

FOREIGN PATENT DOCUMENTS

| | | |
|---|---|---|
| EP | 0350840 A2 | 1/1990 |
| EP | 3300754 A1 | 4/2018 |
| WO | 9512385 A1 | 5/1995 |
| WO | 0066107 A2 | 11/2000 |
| WO | 03039546 A1 | 5/2003 |
| WO | 2005042767 A2 | 5/2005 |
| WO | 2008008373 A2 | 1/2008 |

(Continued)

OTHER PUBLICATIONS

Ortega et al., "Understanding Severe Acute Respiratory Syndrome Coronavirus 2 Replication to Design Efficient Drug Combination Therapies", Published online: Oct. 23, 2020, Intervirology, 63(1-6), pp. 2-9. (DOI: 10.1159/000512141) (Year: 2020).*
Telbisz et al., "Interactions of anti-COVID-19 drug candidates with multispecific ABC and OATP drug transporters", 2021, Pharmaceutics, 13(1), pp. 1-8, (doi.org/10.3390/pharmaceutics13010081) (Year: 2021).*
FDA Notice for Ivermectin and COVID-19. (https://www.fda.gov/consumers/consumer-updates/why-you-should-not-use-ivermectin-treat-or-prevent-covid-19). (Year: 2021).*

(Continued)

*Primary Examiner* — My-Chau T. Tran
(74) *Attorney, Agent, or Firm* — Patterson + Sheridan, LLP

(57) ABSTRACT

The invention concerns a medicine and a prophylactic medicine for COVID-19 disease. The inventive medicine targets the endosomic, non-endosomic and/or intracellular viral pathways and inhibits them. The best mode of the invention is considered to be the medicine that blocks all three viral pathways. In the best mode the individual dose of a constituent component of the medicine is arranged to a dosage size sufficient to inhibit its designated SARS-CoV-2 viral pathway. This allows the dose of a particular pharmacological agent to be smaller than in a drug with just one kind of pharmacological agent. The best mode of the invention shuts the two cell membrane viral pathways and the one intracellular viral pathway with the minimum efficient dose, thereby preventing drug overdose, and enabling prophylactic or preventive use.

7 Claims, 9 Drawing Sheets

(56) References Cited

FOREIGN PATENT DOCUMENTS

| WO | 2008113177 A1 | 9/2008 |
| WO | 2012026963 A2 | 3/2012 |
| WO | 2013044871 A1 | 4/2013 |
| WO | 2018222643 A1 | 12/2018 |
| WO | 2019241213 A1 | 12/2019 |

OTHER PUBLICATIONS

Millet, J.K. et al., "Physiological and Molecular Triggers for SARS-CoV Membrane Fusion and Entry Into Host Cells," Virology. 2018;517:3-8.

Zumla, A. et al., "Coronavirus—drug discovery and therpeutic options," Nat Rev Drug Discov. 2016;15(5):327-347.

Farsalinos, K. et al., "Systematic review of the prevalence of current smoking among hospitalized COVID-19 patients in China: could nicotine be a therapeutic option?," Intern Emerg Med. 2020;1-8.

Farsalinos, K. et al., "Editorial: Nicotine and SARS-CoV-2: COVID-19 may be a disease of the nicotinic cholinergic system," Toxicol Rep. 2020;7:658-663.

National Carrier for Biotechnoiogy Information. "PubChem Compound Summary for CID 14013, Ammonium bicarbonate" PubChem, https:pubchem.ncbi.nlm.gov/compound/Ammonium-bicarbonate. Create Jul. 19, 2005. Accessed Dec. 2, 2020. (Year: 2005).

Ding et al., "Organ distribution of severe acute respiratory syndrome (SARS) associated coronavirus (SARS-Cov) in SARS patients : implications for pathogenesis and virus transmission pathways", 2004, Journal of Pathology, 203(2), pp. 622-630. (Year: 2004).

Ziegler el al., "SARS-CoV-2 Receptor ACE2 Is an Interferon-Stimulated Gene in Human Airway Epithelial Cells and Is Detected in Specific Cell Subsets across Tissues", May 28, 2023, Cell, 181 (5), pp. 1016-1035. (https://doi.org/10.1016/j .cell.2020.04.035) (Year : 2020).

Sungnak et al.,"SARS-CoV-2 entry factors are highly expressed in nasal epithelial cells together with innate immune genes", May 2020, Nature Medicine, 26(5), pp. 681-687. (Year: 2020).

National Institutes of Health (NIH) press release, Jun. 20, 2020, "NIH halts clinical trial of hydroxychloroquine", pp. 1-2. (https://www.nih.gov/news-events/news-releases/nih-halts-cli nical-trial-hydroxychloroquine) (Year: 2020).

Magagnoli et al., "Outcomes of Hydroxychloroquine Usage in United States Veterans Hospitalized with COVI D-19", Nov. 2020, Med, vol. 1, pp. 1-14. (https:/ /doi.org/10.1016/j.medj .2020.06.001) (Year: 2020).

Konstantinos Farsalinos Editorial: Nicotine and SARS-CoV-2:COVID-19 may be a disease of the nicotinic cholinergic system, Toxicology Reports 884, May 2020.

Ibrahim M.Ibrahima, Doaa H.Abdelmaleka, Mohammad E.Elshahata, Abdo A.Elfikyab. COVID- 19 spike-host cell receptor GRP78 binding site prediction, (Journal of Infection vol. 80. Issue 5, May 2020, pp. 554-562).

Hati S, Bhattacharyya S: Impact of Thiol-Disulfide Balance on the Binding of Covid-19 Spike Protein with Angiotensin-Converting Enzyme 2 Recepter ASC Publications, 2020, 5, 16292-16298.

Bojkova, D et al., "Aprotinin Inhibits SARSCoV-2 Replication". Cells. 9 (11):2377. doi:10.3390/cells9112377. ISSN 2073-4409, 2020.

Savarino A et al., "Effects of chloroquine on viral infections: an old drug against today's diseases?". The Lancet. Infectious Diseases. 3 (11): 722-7, doi:10.1016/s1473-3099(03)00806-5, PMC 7128816. PMID 14592503, Nov. 2003.

Xue J, Moyer A, Peng B, Wu J, Hannafon BN. Ding WQ (Oct. 1, 2014). "Chloroquine is a zinc ionophore". PLOS ONE. 9 (10):e109180. Bibcode:2014PLoSO . . . 9j9180X. doi:10.1371/journal.pone. 010918. PMC 4182877. PMI D 25271834.

Te Velthuis AJ, van den Worm SH, Sims AC, Baric RS, Snijder EJ, van Hemert MJ (Nov. 2010). "Zn(2+) inhibits coronavirus and arterivirus RNA polymerase activity in vitro and zinc ionophores block the replication of these viruses in cell culture", PLOS Pathogens, 6 (11): e1001176. doi:10.1371/journal.ppat.1001176. PMC 2973827. PMID 21079686.

An Enzymatic TMPRSS2 Assay for Assessment of Clinical Candidates and Discovery of Inhibitors as Potential Treatment of COVID~19, ACS Pharmacol. Transl. Sci. 2020, 3, 5, 997-1007. Jonathan H Shrimp, Stephen C Kales, Philip E. Sanderson, Anton Simeonov, Min Shen, and Matthew D. Hall.

National Center for Biotechnology Information. "PubChem Compound Summary for CI D 14013, Ammonium bicarbonate" PubChem, <https://pubchem.ncbi.nlm.nih.gov/compound/Ammonium-bicarbonate>. Create Jul. 19, 2005. Accessed Dec. 2, 2020. (Year: 2005).

PCT Notification of Transmittal of the International Search Report and the Written Opinion of the International Searching Authority, of the Declaration for Application No. PCT/F12021/050172 dated Jun. 17, 2021.

Hansen, G.H. et. al., the Coronavirus transmissable Gastroenteritis Virus Causes Infection after Receptor-Mediated Endocytosis and Acid-Dependent Fusion with an Intracellular Compartment, J. Virol. 1998, vol. 72, No. 5, 527-537.

Hoffmann, M. et al., "SARS-CoV-2 cell Entry Depends on ACE2 and TMPRSS2 and Is Blocked by a Clinically Proven Protease Inhibitor," Cell Apr. 16, 2020, vol. 181 ,271-280.

Open Lable Study to Compare Efficacy, Safety and Tolerability of Hydroxychloroquine Combined with Azithromycin Compared to Hydroxychloroquine Combined with Camostat Mesylate and to "no Treatment," in SARS CoV2 Virus (COSTA), ClinicalTrails.gov [Online], Apr. 21, 2020.

Cegolon, L. "Investigating hypothiocyanate against SARS-CoV-2," International Journal of Hygiene and Environmental Health Apr. 6, 2020, vol. 227, 113520.

\* cited by examiner

- Nasal cavity
- Nasopharynx
- Larynx

Upper respiratory tract

- Trachea
- Lung

Lower respiratory tract

300 — Virus contamination

310 — Virus settling

320 — Virus binding a) 330 — Non-endosomic pathway    b) Endosomic pathway — 340

350 — Virus fusion either pH independently or dependently

360 — Virus genome releasing

370 — Virus genome replication

380 — Virus protein synthesis

390 — Virus protein maturation ✗ Inhibition site 3 — 391

392 — Virus assembly and exocytosis

Infection of new cells

Fig. 3

MEDICINE FOR COVID-19 AND TREATMENT

CROSS-REFERENCE TO RELATED APPLICATIONS

This application is a continuation-in-part of U.S. patent application Ser. No. 16/872,108, filed May 11, 2020, which claims priority to U.S. Provisional Patent Application No. 63/015,345, filed Apr. 24, 2020 and 62/994,647, filed Mar. 25, 2020, each of which is incorporated herein by reference in their entireties.

FIELD

The present disclosure is generally related to a medicine and a prophylactic medicine for COVID-19.

BACKGROUND

Viruses are incapable of free-living existence. They can infect cells and cause various diseases by invading cells and redirecting the synthetic machinery of mammalian cells toward the production of more virus particles. Viruses can enter cells via different mechanisms.

In case of respiratory viral diseases, viruses enter body usually via the epithelial cells of respiratory tract. Accompanying FIGS. 1-3 and 7 show anatomical structure of human respiratory tract. Often viruses enter the body already through epithelial cells in upper respiratory tract, for instance via nasal mucosa. This is true especially if viruses are delivered by accident via hands to nasal mucosa.

When the virus has reached the surface of respiratory epithelium, it must enter the cell in order to propagate the disease.

First, the virus needs a specific cellular receptor on plasma membrane. Several specific receptors for different viruses are known. However, usually each virus has only one specific type of receptor on the target cell membrane. Receptors could be proteins, carbohydrate moieties or even membrane lipids. In case of influenza A the virus specific receptor is alpha-2,6-sialic acid and in case of SARS-Cov and SARS-Cov-2 the specific receptor is the ACE2 protein.

After binding of the virus to the specific membrane protein, for example, this binding induces a cascade of molecular events that eventually lead to the release of viral genome into the host cell cytoplasm. The presence of a specific receptor on the cell surface is usually needed for viral entrance. After binding to the cell membrane, different viruses can induce one or even more molecular mechanisms to enter the cellular cytoplasm as indicated in accompanying figures.

SARS-Cov-2 virus that induces human Covid-19 disease can either perform a so-called early entry (FIGS. 1 and 4) or late entry (FIGS. 2 and 5) into cellular cytoplasm.

In the early entry, specific cellular proteases are needed to cleave the viral protein, which will activate the fusion of viral envelope to the cell membrane and lead to entry of viral nucleocapsid into cellular cytoplasm.

In case of influenza and corona viruses, activating proteases could be at least transmembrane protease serine S1 member and human trypsin like protease. In addition to endogenous proteases, also other proteases secreted into the luminal space could induce cleavage and activate the fusion of virus envelope to the plasma membrane.

Enveloped viruses like influenza and corona viruses can enter the epithelial cells also via receptor-mediated endocytosis and release viral content in late endosomes. This type of entry does not need proteases on the cell surface.

In this type of endosome entrance into cytoplasm virus attaches to a specific type membrane receptor and this binding induces so called receptor-mediated endocytosis. Virus particles are taken first into early endosomes and during maturation of these towards late endosomes, and the interiors of these vesicles becomes acidic via action of membrane bound vacuolar ATPase. This acidification activates endosomal proteases, like cathepsin L. Activated proteases are able to cleave viral envelope inducing fusion of virus to the late endosome's membrane and leading to the release of viral genome into cellular cytoplasm.

After releasing of viral genome into the cytoplasm, copying the genome with reverse transcriptase enzyme (depending on the genomic material type), synthesizing virus genome and proteins by cellular machinery, virus genome and virus proteins are assembled to form new viruses, which can then propagate the infection further. Viral protein genes are translated to proteins via cellular protein synthesis machinery in endoplasmic reticulum and Golgi complex.

It is known in the art that people who work with cattle rarely contract influenza.

Washing hands with soap is also known to be a good strategy to prevent viruses.

Four human coronavirus strains (HCoV-229E, HCoV-OC43, HCoV-NL-63 and HCoV-HKU1) are known in the art, which cause mild upper respiratory tract infections. However, during last 20 years two new zoonotic coronaviruses have appeared, MERS-CoV (Middle East respiratory syndrome coronavirus) and SARS-CoV (severe acute respiratory syndrome coronavirus). By contrast to human coronaviruses, these can cause more severe disease symptoms, mainly in respiratory organs, but also extrapulmonary complications. In 2019 a third zoonotic coronavirus emerged, SARS-CoV-2 causing the COVID-19 disease (also called COVID-19 virus).

Millet, et al. (1) describes the strategies of coronavirus entry into cells. Coronavirus enters into cell by two alternative routes: non-endosomic and/or endosomic pathways. In non-endosomic entry virus particle attaches to host cell membrane through virus surface S protein (spike) and specific cell membrane ACE2 (angiotensin-converting enzyme) receptor interaction. Then S protein fuses virus envelope to cell membrane by the aid of cell proteinases in a pH independent way, virus enters into cell, dissembles and releases its genome (RNA) into cytoplasm. Thereafter the released uncoated RNA is replicated by reverse transcriptase enzyme and virus protein synthesis and replication of new virus genomic RNA starts and proceeds by host's cellular machinery. Virus proteins are transported through endoplasmic reticulum/Golgi apparatus, where they mature in pH dependent conditions, e.g. by glycosylation. Then virus particles are assembled from virus proteins and virus RNA genome in the cytoplasm to new infectious viruses. Finally, viruses are released from the cell by exocytosis and infect new cells. In endosomic entry, virus particle attaches to host cell membrane also through virus surface S protein (spike) and specific cell membrane ACE2 receptor interaction, like above. After that, the virus is taken into cell early endosome by clathrin-mediated endocytosis. When early endosome acidifies to mature late endosome, virus fuses to endosome's membrane through S protein/ACE2 interaction and by the aid of cellular proteinases. Then RNA genome is released into cytoplasm, and from this point, the production and maturation of virus particles are identical to non-endosomic pathway. These strategies are depicted in more detail in accompanying figures.

There are many stages, where the entry of the virus, the release of its genome and its maturation can be prevented, although currently there is no antiviral treatment effective for coronaviruses. At the time of writing, there is a suspicion that Remdesivir developed by Gilead Sciences might have some efficacy against the coronavirus in very ill patients, reducing the time spent per patient in Intensive Care Units ICU.

Zumla, et al. (2) reviews numerous therapeutic interventions suggested and studied in clinical trials. These include e.g. virus-based strategies to disturb/prevent replication of the virus RNA genome, to inhibit synthesis and function of different virus proteins and to prevent virus S protein/cell ACE2 receptor interaction, or host-based strategies to induce host's immune response, to prevent host signaling pathways involved in virus replication, to inhibit virus entry by blocking cellular receptors or by inhibiting the function of cellular membrane and endosomal proteins, by disturbing endocytosis or by modifying cell's pH levels at different stages. Also, studies to develop vaccines have been numerous and extensive by different design strategies, but with no clinical success yet.

US20140311482 A1 (3) lists a broad catalogue of treatments that can be administered with a broad array of drug delivery strategies. It relates to the treatment of upper airway infections with proinflammatory cytokine inhibitors and other bioactive agents, like antiangiogenic, anti-inflammatory, antibiotic, antiviral, antifungal and antiprotozoal compounds, focusing on their usage in the treatment of sinusitis. In addition, it describes the use of different drug delivery systems for local noninvasive administration of the drugs to nasopharyngeal tract. These include nasal administration e.g. by sprays, aerosols, gels, solutions, emulsions and suspensions, and with the aid of targeting delivery devices, like nasal inhalers, aerolizers and microcatheters.

Farsalinos et al. Toxicology Reports 884 have analyzed ACE2 receptor and nicotin. However this publication does not disclose any mechanics or chemistry related to viral passage via endocytosis on the cell membrane.

In the prior art both the intracellular and the extracellular pathways with which coronavirus interacts with the mammalian cells are reasonably well understood. There are several studies and trials going on to develop new drugs and vaccines to prevent or treat COVID-19, but no effective cure or preventive measure for it has yet been found.

SUMMARY

One aspect of the invention is a medicine that comprises at least one protease inhibitor arranged to inhibit the fusion of the COVID-19 virus through the plasma membrane of a mammalian respiratory cell (see inhibition site 1, FIGS. 1 and 4).

Another second aspect of the invention is a medicament for altering the pH of the mammalian respiratory cell endosomal interior in order to inhibit the passage of the COVID-19 through the endosomal membrane into the cell cytoplasm.

In one embodiment, the pH is increased, so that the environment of the endosome is more basic. In one embodiment, the medicine is a nasal spray, such as chloroquine phosphate.

Alternative drug administration methods include orally consumed pills, chewing gum and/or creams or any other local application method that increases the pH in the respiratory cell membranes and endosomes.

Alternative embodiments may use hydroxychloroquine phosphate and/or chloroquine phosphate and/or chloroquine sulphate and/or hydroxychloroquine sulphate as the pH increase inducing agent.

The activation of late endosomal proteases can be inhibited by preventing acidification of endosomes. This could be done by weak bases like chloroquine, ammonium salts or by blocking vacuolar ATPase by proton pump inhibitors, like bafilomycin. Acidification can also be disturbed by affecting ion channels, e.g. glutamate gated chloride channels, by ivermectin.

The inhibition of endosomal acidification can thus prevent replication of viruses via receptor-mediated endocytosis (see inhibition site 2, FIGS. 2 and 5).

In another third aspect of the invention in late compartments of Golgi complex, slightly acidic pH is needed for proper glycosylation of proteins. In virus-infected cells, basically all protein synthesis serves production of viral proteins. If one could prevent acidification of the trans-Golgi network of infected cells, the infected cells would not be able to glycosylate viral proteins correctly. This acidification can be prevented by weak bases and vacuolar proton pump inhibitors, and thus giving another possibility to inhibit new virus formation (see inhibition site 3, FIGS. 3 and 6). This block will inhibit synthesis of viral proteins entering cells by all possible pathways.

A medicine for COVID-19 and other viruses (such as respiratory tract viruses), characterized in that, the medicine comprises at least one protease inhibitor arranged to inhibit the fusion of the COVID-19 virus through the plasma membrane of a mammalian respiratory cell.

A medicine for COVID-19 and other viruses (such as respiratory tract viruses) is in accordance with the invention and characterized in that, the medicine is a pH increase inducing agent, and said medicine is administered to a patient to inhibit endosomal acidification, thereby preventing cathepsin activation and inhibiting fusion of viral envelope to the endosomal membrane thus preventing release of SARS-CoV-2 viruses into the cytoplasm and the consequent replication of SARS-CoV-2 viral RNA in the mammalian respiratory cell.

A medicine for COVID-19 and other viruses (such as respiratory tract viruses), characterized in that,
  the medicine is arranged to target viral RNAs in the endoplasmic reticulum, and/or
  the viral RNAs are arranged to be translated to viral proteins, and the viral proteins are arranged to be transported into the Golgi compartment of the mammalian respiratory cell, where the viral proteins are arranged to be glycosylated, and/or
  the medicine is arranged to inhibit any of the preceding reactions and/or arranged to inhibit proton pumps.

A medicine for COVID-19 and other viruses (such as respiratory tract viruses) is in accordance with the invention and is characterized in that,
  the medicine is a pH increase inducing agent, and said medicine is administered to a patient to inhibit endosomal acidification preventing cathepsin activation and thus inhibit fusion of viral envelope to the endosomal membrane preventing release of SARS-CoV-2 viruses into the cytoplasm, and the consequent replication of SARS-CoV-2 viral RNA in the mammalian respiratory cell, and/or the medicine comprises protease inhibitors arranged to inhibit the fusion of the SARS-CoV-2 virus through the plasma membrane of a mammalian respiratory cell, and/or the medicine is arranged to target viral RNAs in the endoplasmic reticulum, and/or the viral RNAs are arranged to be translated to viral proteins, and the viral proteins are arranged to be transported into the Golgi compartment of the mammalian respiratory cell, where the viral proteins are arranged to be glycosylated, and/or the medicine is arranged to inhibit any of the preceding reactions and/or arranged to inhibit proton pumps.

The invention has great advantages in that it can be used to prevent a COVID-19 infection when social contact is unavoidable and/or necessary. Because the inventive medicine is targeted to all viral pathways, the absolute doses of the constituent medicines can be small, thus allowing long term use even for people who might be sensitive to the constituent medicines in normal doses. This allows healthcare workers, such as doctors and nurses, to consume the inventive medicine all the time when they are in contact with patients. The medicine also has the advantage over hygienic measures in that the effect is on all the time. Many healthcare workers who have worn protective gear have fallen ill, because the coronavirus has "leaked" through the protective gear.

The best mode of the invention is considered to be the medicine that blocks all three viral pathways. In the best mode, the individual dose of a constituent component of the medicine is arranged to a dosage size sufficient to inhibit its designated SARS-CoV-2 viral pathway. This allows the dose of a particular pharmacological agent to be smaller than in a drug with just one kind of pharmacological agent. The best mode of the invention shuts the two plasma membrane viral pathways and the one intracellular viral pathway with minimum efficient dose, thereby preventing drug overdose, and enabling prophylactic or preventive use.

BRIEF DESCRIPTION OF THE DRAWINGS

Figure 2:
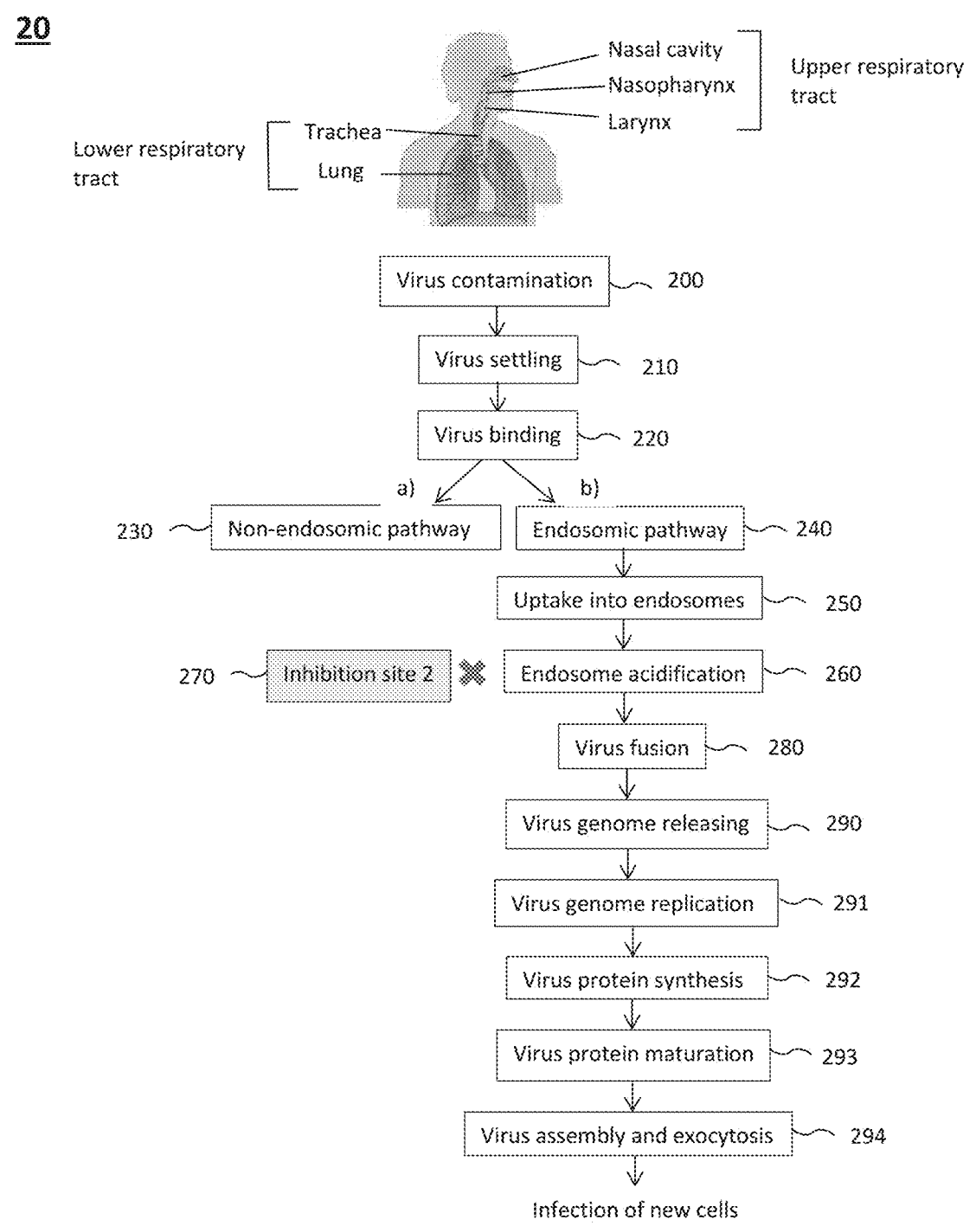

FIG. 2 shows the anatomical structure of human respiratory tract. It also describes the virus entry via endosomic pathway into a mammalian respiratory cell cytoplasm as an embodiment 20 as a flow diagram, and the inventive medicine impact to said viral pathway, in accordance with the invention (inhibition site 2, phase 270).

FIG. 3 shows the anatomical structure of human respiratory tract. It also describes the virus intracellular viral pathway in the endoplasmic reticulum and Golgi complex of a mammalian cell as an embodiment 30 as a flow diagram, and the inventive medicinal impact to this viral pathway, in accordance with the invention (inhibition site 3, phase 391).

Some embodiments of the invention are described in the dependent claims.

DETAILED DESCRIPTION

The invention is illustrated in more detail in the following figures.

Figure 1:
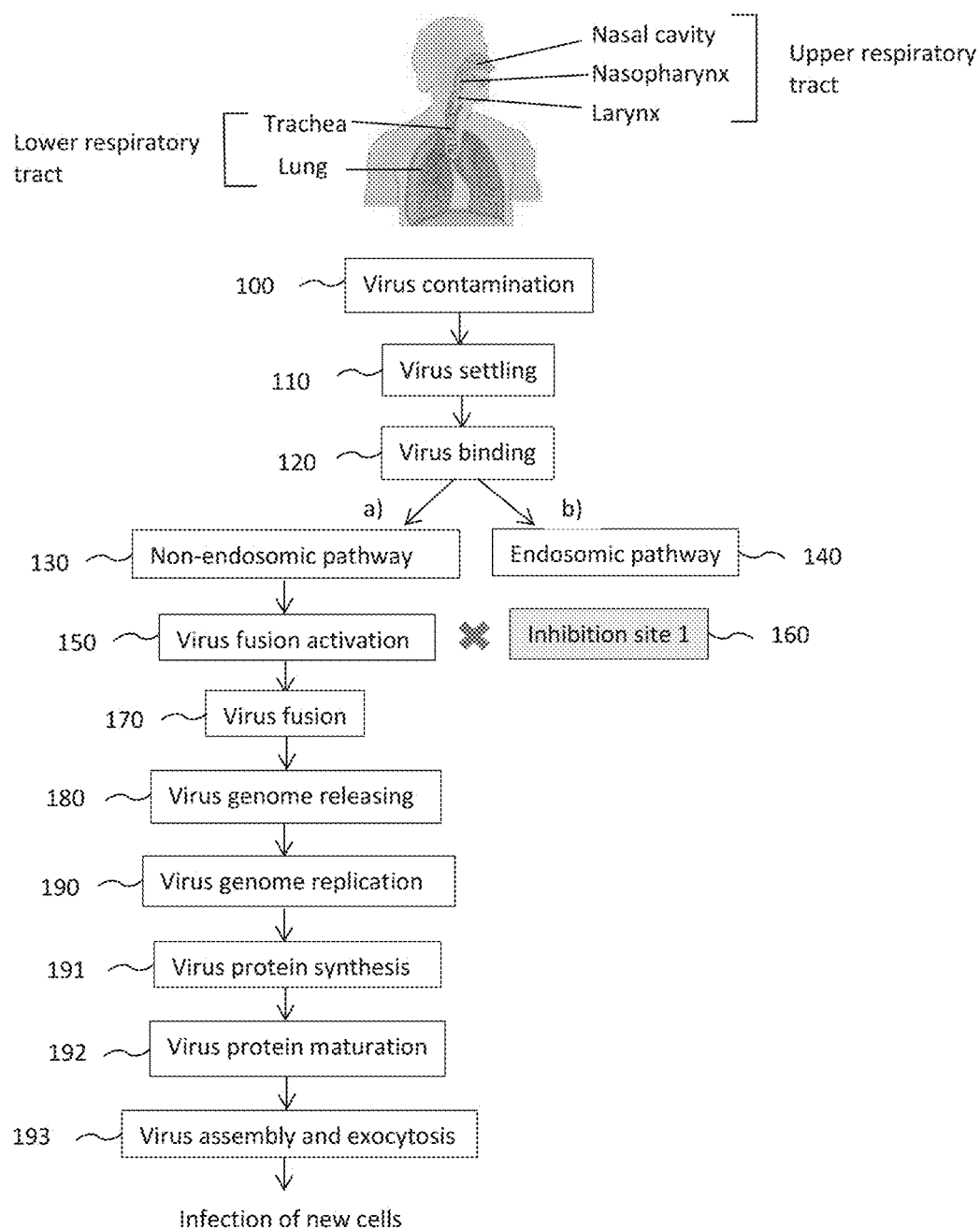
FIG. 1 shows the anatomical structure of human respiratory tract. It also describes the virus entry via non-endosomic pathway into a mammalian respiratory cell cytoplasm as an embodiment 10 as a flow diagram, and the inventive medicine impact to said viral pathway, in accordance with the invention (inhibition site 1, phase 160).

FIG. 1 displays the embodiment 10, where in phase 100 enveloped viruses, like coronavirus, enter and contaminate the respiratory tract either via direct contact of fingers or other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 110 after contamination 100 virus approaches and settles down on respiratory tract mucosa. To initiate infection virus has to enter into epithelial cells of the respiratory mucosa.

In phase 120 after settling 110 on cell membrane, virus binds to a specific receptor on the surface of respiratory tract epithelial cells. Each enveloped virus has its own specific receptor for binding. For SARS-CoV-2 this receptor is ACE2 membrane protein. E.g. for influenza it is alpha-2,6-sialic acid. In the case of SARS-CoV-2, this binding happens through virus surface S protein (spike) and cell membrane ACE2 receptor interaction.

After SARS-CoV-2 virus binding 120 to cell membrane receptor, two alternative pathways 130 and 140 can be initiated: a) non-endosomic pathway 130 (endocytosis independent pathway), or b) endosomic pathway 140 (endocytosis dependent pathway). Depending on the virus, for the entry into cell, it can use either pathways a) or b); in the case of coronavirus, it can use both of them.

The embodiment 10 describes the pharmaceutical effect of the invention on the non-endosomic pathway 130. In the non-endosomic pathway (a) 130 membrane protease, e.g. transmembrane protease serine subfamily 2 (TMPRSS2), activates the ACE2 receptor and virus S protein for fusion in phase 170 in pH independent manner. This activation can be inhibited at inhibition site 1 160 by protease inhibitors, e.g. camostat and aprotinin. This is the reason that the inventive medicine preferably contains meaningful doses of protease inhibitors, e.g. camostat and aprotinin.

In phase 170 protease activates a fusion peptide part in the virus S protein, which then fuses virus envelope into the cell membrane.

In phase 180, after fusion 170, virus nucleocapsid enters into cell cytoplasm and dissembles, whereby virus genetic material is released. In the case of coronaviruses, the genetic material is a single-stranded RNA genome.

In phase 190 after genome releasing 180 of virus genome, the virus genome replicates by reverse transcriptase enzyme in the case of SARS-Cov-2, produced by host cell's protein synthesis machinery.

In phase 191 viral proteins and RNA genome of SARS-CoV-2 are synthesized using host cell's own protein synthesis machinery. At this point virus 'kidnaps' for its use the whole protein producing capacity of the cell and most of the products synthesized are viral (proteins, RNA).

In phase 192 after viral protein synthesis 191, the viral proteins are maturated in host cell's endoplasmic reticulum/Golgi compartment, e.g. by glycosylation. Some of these protein maturation reactions in Golgi apparatus are pH dependent (acidic).

In phase 193, after viral protein maturation 192, these viral proteins and new genomic viral RNA molecules 190 are assembled in the cytoplasm to give rise to new infectious virus particles. After assembly, virus particles are released from the cell by exocytosis and initiate the infection cycle in new cells.

The inventive medicine targets the virus fusion phase 170 and the virus fusion activation phase 150 by providing viral fusion inhibiting protease inhibitors, e.g. camostat and aprotinin. When phases 150 and 170 become inactive, the virus production machine of the host cell phases (180, 190, 191, 192, 193) does not start, as new SARS-CoV-2 viruses cannot enter via the non-endosomic pathway 130. These protease inhibitor compounds are preferably locally administered to the patients by means of any of the following: Nasal drops, nasal sprays or aerosols targeted into lower respiratory pathway, either alone or in combinations. For example, in some embodiments the inventive medicine could be vaporized or provided as an aerosol through the air conditioning system or air ventilation system of a building, for example a hospital.

However, the SARS-CoV-2 can still enter the host cell via the endosomic pathway and this is discussed in FIG. 2, embodiment 20.

Embodiment 10 can be readily combined with embodiments 20, 30, 40, 50, 60, 70, 80 and/or 90, because the intracellular and extracellular pathways described therein are in use simultaneously in a mammalian respiratory cell, in accordance with the invention.

In FIG. 2 phase 200 the coronavirus enters and contaminates the respiratory tract. The coronavirus obtains access either via direct contact of fingers or via direct contact form other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 210, after contamination 200 virus approaches and settles down on respiratory tract mucosa. To initiate infection virus has to enter into epithelial cells of the respiratory mucosa.

In phase 220 after settling in phase 210 on cell membrane, virus binds to specific receptor on the surface of respiratory tract epithelial cells. Each enveloped virus has its own specific receptor for binding. For SARS-CoV-2 this receptor is ACE2 membrane protein. In the case of SARS-CoV-2 this binding happens through virus surface S protein (spike) and cell membrane ACE2 receptor interaction.

After virus binding 220 to cell membrane receptor, two alternative pathways 230 and 240 can be initiated: a) non-endosomic pathway 230 (endocytosis independent pathway), orb) endosomic pathway 240 (endocytosis dependent pathway). This embodiment 20 focuses on the endosomic pathway. Depending on the virus, for the entry into cell, it can use either pathways a) or b); in case of coronavirus, it can use both of them.

In phase 250 in endosomic pathway (b) 240 after virus has bound to ACE2 on cell membrane, ACE2/virus complex is transferred into an early endosome through a clathrin-mediated endocytosis.

In cytoplasm, the early endosome is acidified and matures to late endosome. This acidification in phase 260 can be inhibited at inhibition site 2 in phase 270 by weak bases, like ammonium salt, ammonium chloride, ammonium bicarbonate and chloroquine, by vacuolar ATPase inhibitors, like bafilomycins and diphyllin, or by ion channel modulators, like ivermectin. The inventive medicine preferably comprises any of the aforementioned compounds in meaningful doses to inhibit the endosome acidification, and the transport of the ACE2/SARS-CoV-2 complex within the endosome.

In phase 280 acidification of the endosome 260 causes the virus to fuse to endosome membrane through the interaction of ACE2 receptor and virus S protein fusion peptide activated by protease, like cathepsin, in acidic pH conditions.

In phase 290 after fusion 280, virus nucleocapsid enters into cell cytoplasm and dissembles, whereby virus genetic material is released. In the case of coronaviruses, the genetic material is a single-stranded RNA genome.

In phase 291 after genome releasing 290 of virus genome, it replicates by reverse transcriptase enzyme in the case of SARS-Cov-2, produced by host cell's protein synthesis machinery.

In phase 292 viral proteins and RNA genome, in the case of SARS-CoV-2, are synthesized using host cell's own protein synthesis machinery. At this point SARS-CoV-2 'kidnaps' for its use all or some of the protein producing capacity of the cell and most of the products synthesized are viral proteins and viral RNA.

In phase 293 after viral protein synthesis 292, they are maturated in host cell's endoplasmic reticulum/Golgi compartment, e.g. by glycosylation. Some of these protein maturation reactions in Golgi apparatus are pH dependent (acidic).

In phase 294 after viral protein maturation 293, they and new genomic viral RNA molecules 291 are assembled in the cytoplasm to form new infectious virus particles. After assembly, virus particles are released from the cell by exocytosis and can initiate the infection cycle in new cells. When phase 260 becomes inactive, the virus production machine of the host cell phases (280, 290, 291, 292, 293) does not start, as new SARS-CoV-2 viruses cannot enter via the endosomic pathway 240. These weak bases, vacuolar ATPase inhibitors and/or by ion channel modulators compounds are preferably locally administered to the patients by means of any of the following: Nasal drops, nasal sprays or aerosols targeted into lower respiratory pathway, either alone or in combinations. For example, in some embodiments the inventive medicine could be vaporized or provided as an aerosol through the air conditioning system or air ventilation system of a building, for example a hospital.

Even more preferably the weak bases, like ammonium bicarbonate and chloroquine, by vacuolar ATPase inhibitors, like bafilomycins and diphyllin, or by ion channel modulators, like ivermectin of phase 270 are mixed together with protease inhibitors, such as camostat and aprotinin, used in phase 130 of embodiment 10. This will preferably lead to complete blocking of SARS-CoV-2 viruses from the respiratory cells, as the SARS-CoV-2 cannot penetrate the cell membrane of the respiratory cell. The doses of each of the aforementioned compounds should preferably be set to a level, that results in complete SARS-CoV-2 blocking. However, dosages at that level might be unattainable in some patients, and there may be some random error in that no matter what the doses at inhibiting phases 130, 270, some SARS-CoV-2 viruses manage to enter the cytoplasm. Or worse, there might be a third yet undiscovered extracellular pathway that we do not presently know about.

Therefore, we will look at an inventive intracellular inhibiting mechanism in FIG. 3, embodiment 30.

Embodiment 20 can be readily combined with embodiments 10, 30, 40, 50, 60, 70, 80 and/or 90, because the intracellular and extracellular pathways described therein are in use simultaneously in a mammalian respiratory cell, in accordance with the invention.

In FIG. 3 embodiment 30 enveloped viruses, like the coronavirus, enter and contaminate the respiratory tract either via direct contact of fingers or other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 310 after contamination 300 virus approaches and settles down on respiratory tract mucosa. To initiate infection virus has to entry into epithelial cells of the respiratory mucosa.

In phase 320 after settling in phase 310 on cell membrane, SARS-CoV-2 virus binds to specific receptor on the surface of respiratory tract epithelial cells. Each enveloped virus has its own specific receptor for binding. For SARS-CoV-2 this receptor is ACE2 membrane protein, and e.g. for influenza it is alpha-2,6-sialic acid. In the case of SARS-CoV-2, this binding happens through virus surface S protein (spike) and cell membrane ACE2 receptor interaction.

After virus binding 320 to cell membrane receptor, two alternative pathways 330 and 340 can be initiated: a) non-endosomic pathway 330 (endocytosis independent pathway), or b) endosomic pathway 340 (endocytosis dependent pathway). Depending on the virus, for the entry into cell, it can use either pathways a) or b); in case of SARS-CoV-2, it can use both of them.

In phase 350 the SARS-CoV-2 nucleocapsid fuses to cell membranes either in pH independent way 170 to cell membrane or in pH dependent way 280 to endosomal membrane.

In phase 360, after fusion 350, the SARS-CoV-2 virus nucleocapsid enters into cell cytoplasm and dissembles, whereby viral genetic material is released. In the case of SARS-CoV-2, the genetic material is a single-stranded RNA genome.

In phase 370 after genome releasing in phase 360 of SARS-CoV-2 virus genome, it replicates by reverse transcriptase enzyme produced by host cell's protein synthesis machinery.

In phase 380 viral proteins and RNA genome, in the case of SARS-CoV-2, are synthesized using host cell's own protein synthesis machinery. At this point SARS-CoV-2 virus tries to 'kidnap' for its use the whole protein producing capacity of the cell which would lead to most of the products being synthesized being viral (proteins, RNA).

After viral protein synthesis 380 they are maturated in host cell's endoplasmic reticulum/Golgi compartment, e.g. by glycosylation. Some of these protein maturation reactions in Golgi apparatus are pH dependent (acidic). This maturation can be inhibited at inhibition site 3 in phase 391 by weak bases, like ammonium salt, ammonium chloride, ammonium bicarbonate and chloroquine. Also, vacuolar ATPase inhibitors, like bafilomycins and diphyllin, or ion channel modulators, like ivermectin, can be used in inhibiting this step. The inventive medicine preferably comprises any of the aforementioned compounds in meaningful doses to prevent and inhibit the viral protein maturation of SARS-CoV-2.

However, in phase 392 after viral protein maturation 390, these viral proteins and new genomic RNA molecules 370 are assembled in the cytoplasm to form new infectious virus particles. Therefore, the inventive medicine aims to inhibit viral protein maturation so that as few new SARS-CoV-2 viruses would eventually be produced by the host cell. After assembly, those virus particles that eventually formed correctly despite the inventive medicine, are released from the cell by exocytosis and can initiate the infection cycle in new cells.

When phase 390 becomes inactive by the inhibiting effect of the inventive medicine, the virus production machine of the host cell cannot produce mature viral proteins, as SARS-CoV-2 viral protein maturation is inhibited in the host cell protein synthesis machinery.

These weak bases, vacuolar ATPase inhibitors and/or by ion channel modulators compounds are preferably locally administered to the patients by means of any of the following: Nasal drops, nasal sprays or aerosols targeted into lower respiratory pathway, either alone or in combinations. For example, in some embodiments the inventive medicine could be vaporized or provided as an aerosol through the air conditioning system or air ventilation system of a building, for example a hospital.

Even more preferably the weak bases, like ammonium salt, ammonium chloride, ammonium bicarbonate and chloroquine, vacuolar ATPase inhibitors, like bafilomycins and diphyllin, or ion channel modulators, like ivermectin of phases 360, 270 are mixed together with protease inhibitors, such as camostat and aprotinin, used in phase 130 of embodiment 10.

Thus, preferably the inventive medicine of this embodiment 30 is combined with cell membrane penetration inhibiting medicines of earlier embodiments 10 and 20. This will result in an inventive combined therapeutic effect on SARS-CoV-2 in the respiratory cell: Both the endosomic and non-endosomic pathways are blocked for SARS-CoV-2, and even if SARS-CoV-2 were somehow able to enter the cytoplasm, its protein maturation is inhibited in the host cell protein synthesis machinery by the inventive medicine.

Embodiment 30 can be readily combined with embodiments 10, 20, 40, 50, 60, 70, 80 and/or 90, because the intracellular and extracellular pathways described therein are in use simultaneously in a mammalian respiratory cell, in accordance with the invention.

Figure 4:
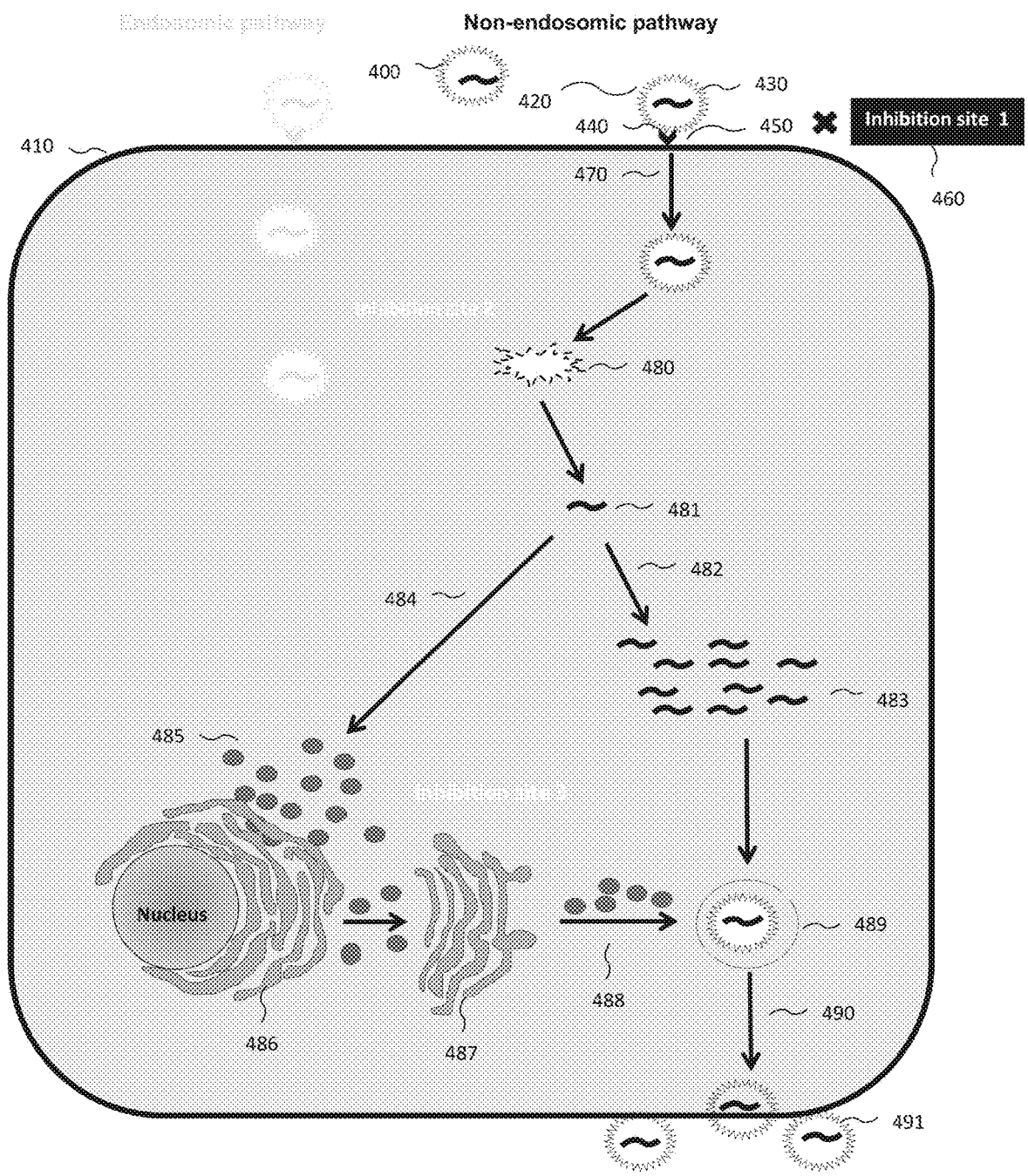
FIG. 4 describes the virus entry via non-endosomic pathway into a mammalian respiratory cell cytoplasm as an anatomic diagram, and the inventive medicine impact to said viral pathway embodiment 40, in accordance with the invention (inhibition site 1, 460).

In the next FIG. 4 we will discuss what embodiment 10 looks like anatomically.

This embodiment 40 FIG. 4 depicts at cellular level the non-endosomic virus entry to the cell from its binding to its release out of cell as an embodiment 40, and shows the impact site (inhibition site 1) of the inventive medicine for inhibiting the propagation of the SARS-CoV-2 virus in to the cell.

After virus 400 has contaminated subject's respiratory tract, it approaches the cell membrane 410 as illustrated in phases 100, 200, 300, settles and binds on cell surface 420 to cellular receptor as illustrated in phases 110, 120, 210, 220, 310, 320. In the case of SARS-Cov-2 virus, this happens through the interaction of virus S protein 430 and cellular receptor ACE2 440. After binding a non-endosomic entry can initiate as illustrated in phases 130, 230, 330.

In the non-endosomic pathway, as illustrated in phases 130, 330, proteases activate in pH independent manner the S protein fusion peptide, which directs the virus envelope to fuse 450 into cell membrane 410, as illustrated in phases 150, 170, 350. This fusion activation can be prevented at inhibition site 1 460 with proteinase inhibitors, such as camostat and aprotinin, as illustrated in phase 160. After fusion the virus 400 enters 470 into cellular cytoplasm and dissembles 480, releasing virus genome 481 (in the case of SARS-CoV-2 the genome is single stranded RNA), as illustrated in phases 180, 360.

The released virus genome 481 is then replicated 482 to new viral genomes 483 by cell's own machinery, as illustrated in phases 190, 370. At the same time, the revealed virus genome 481 also initiates the synthesis of viral proteins 485 by cell's own protein synthesis machinery 484, as illustrated in phases 191, 380. These proteins are synthesized in endoplasmic reticulum 486 and are transported into Golgi apparatus 487, where they maturate to final proteins 488 at partly acidic conditions, as illustrated in phases 192, 390. After Golgi apparatus 487, the mature viral proteins 488 and the replicated new viral SARS-CoV-2 genomes 483 are assembled 489 to new virus particles 491, which are thereafter released from the cell by exocytosis 490, as illustrated in phases 193, 392.

The released viruses 491 can then infect new cells and start the infection cycle again. However, it is clearly apparent that the whole activity within the cell membrane 410

Embodiment 40 can be readily combined with embodiments 10, 20, 30, 50, 60, 70, 80 and/or 90, because the intracellular and extracellular pathways described therein are in use simultaneously in a mammalian respiratory cell, in accordance with the invention.

Figure 5:
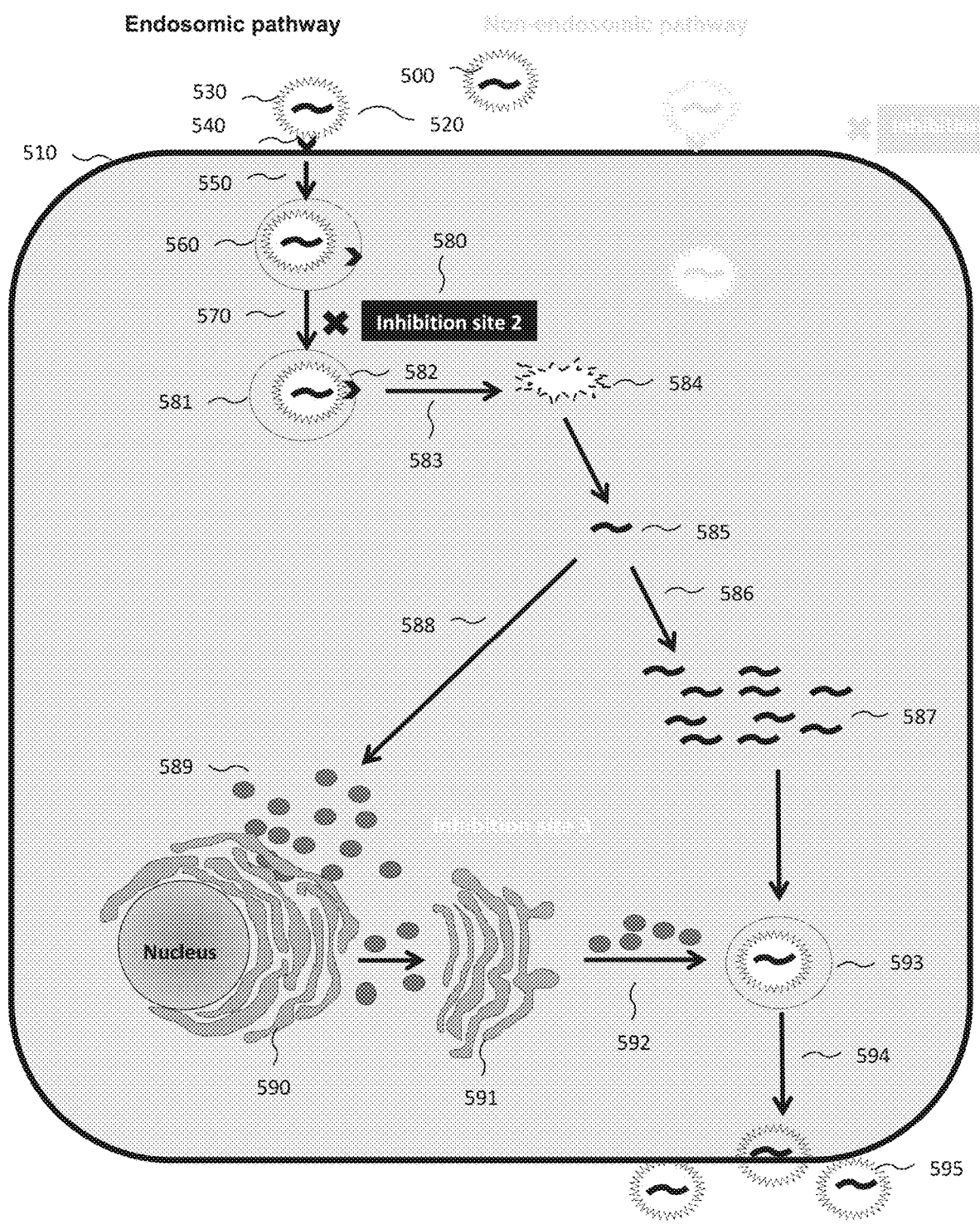
FIG. 5 describes the virus entry via endosomic pathway into a mammalian respiratory cell cytoplasm as an anatomic diagram, and the inventive medicine impact to said viral pathway as embodiment 50, in accordance with the invention (inhibition site 2, 580).

This FIG. 5 depicts at cellular level the endosomic virus entry to the cell from its binding to its release out of cell as an embodiment 50, and shows the impact site (inhibition site 2) of the inventive medicine for inhibiting the propagation of the virus into the cell.

After virus 500 has contaminated subject's respiratory tract, it approaches the cell membrane 510 as illustrated in phases 100, 200, 300, settles and binds 520 on cell surface to cellular receptor as illustrated in phases 110, 120, 210, 220, 310, 320. In the case of SARS-Cov-2 virus, this happens through the interaction of virus S protein 530 and cellular receptor ACE2 540. After binding, an endosomic entry of SARS-Cov-2 virus can initiate as illustrated in phases 140, 240, 340.

In endosomic pathway, as illustrated in phases 240, 340, after binding the virus 500 enters into cell by clathrin-mediated endocytosis 550, where the virus together with ACE2 receptor is uptaken into early endosome 560, as illustrated in phase 250. This early endosome later acidifies 570 by the function of lysosomes to late endosome 581, as illustrated in phase 260. This acidification can be inhibited at inhibition site 2 by the inventive medicine shown by 580.

The inventive medicine causing the inhibiting effect at location 580 in the cell typically comprises any of the following: weak bases, proton pump inhibitors and ion channel inhibitors, as illustrated in phase 270.

After the acidification, proteinases, like cathepsin, activate virus S protein 530 fusion peptide, which through interaction with ACE2 receptor 540 fuses 582 to endosomal membrane, as illustrated in phase 280. After fusion, SARS-CoV-2 virus 500 enters 583 into cellular cytoplasm from the late endosome 581 and dissembles 584, releasing virus genome 585 single stranded RNA, as illustrated in phases 290, 360. This endosomal fusion through the cell membrane into the cytoplasm can be inhibited by the inventive medicine containing for example weak bases, like ammonium salt, ammonium chloride, ammonium bicarbonate and chloroquine, by vacuolar ATPase inhibitors, like bafilomycins and diphyllin, or by ion channel modulators, like ivermectin, in any combination or just individually and separately.

The released virus genome 585 is then replicated 586 to new viral genomes 587 by the cell's own machinery, as illustrated in phases 291, 370. At the same time, the revealed virus genome 585 also initiates the synthesis 588 of viral proteins 589 by cell's own protein synthesis machinery, as illustrated in phases 292, 380.

These proteins are synthesized in endoplasmic reticulum 590 and are transported into Golgi apparatus 591, where they maturate to final proteins 592 at partly acidic conditions, as illustrated in phases 293, 390. After Golgi apparatus 591, the mature viral proteins 592 and the replicated new viral SARS-CoV-2 genomes 587 are assembled 593 to new SARS-CoV-2 virus particles 595, which are thereafter released from the cell by exocytosis 594, as illustrated in phases 294, 392.

These released viruses 595 can then infect new cells and start the infection cycle again.

Embodiment 50 can be readily combined with embodiments 10, 20, 30, 40, 60, 70, 80 and/or 90, because the intracellular and extracellular pathways described therein are in use simultaneously in a mammalian respiratory cell, in accordance with the invention.

Figure 6:
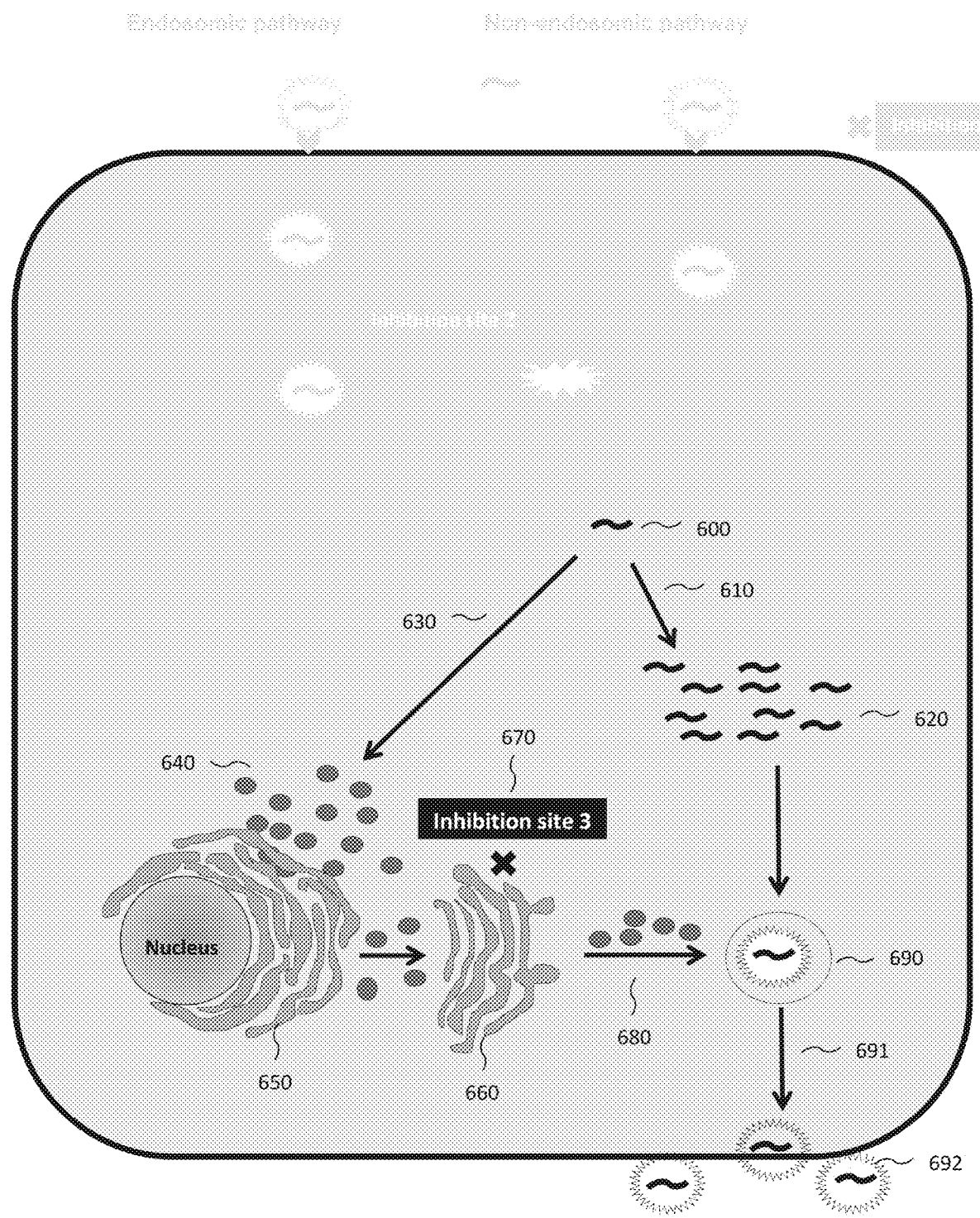
FIG. 6 describes the virus intracellular viral pathway in the endoplasmic reticulum and Golgi complex of a mammalian cell as an anatomic diagram, and the inventive medicinal impact to this viral pathway as an embodiment 60, in accordance with the invention (inhibition site 3, 670).

This FIG. 6 depicts at cellular level the intracellular viral pathway from the released virus genome to virus release out of cell as an embodiment 60, and shows the impact site (inhibition site 3) of the inventive medicine for inhibiting the propagation of the SARS-CoV-2 virus protein synthesis within the host cell.

After the virus genome 600 (in the case of SARS-CoV-2 the genome is single stranded RNA), either after non-endosomic entry, as illustrated in phases 130, 230, 330, or after endosomic entry, as illustrated in phases 140, 240, 340, has been released, as illustrated in phases 180, 290, 360, the virus genome 600 is replicated 610 to new viral genomes 620 by cell's own machinery, as illustrated in phases 190, 291, 370. At the same time, the revealed virus genome 600 also initiates the synthesis 630 of SARS-CoV-2 viral proteins 640 by cell's own protein synthesis machinery, as illustrated in phases 191, 292, 380. These proteins are synthesized in endoplasmic reticulum 650 and are transported into Golgi apparatus 660, where they maturate to final proteins 680 at partly acidic conditions, as illustrated in phases 192, 293, 390.

This maturation can be inhibited by the inventive medicine at inhibition site 3 670 with weak bases, proton pump inhibitors and ion channel inhibitors, as illustrated in phase 391. After Golgi apparatus 660, the mature viral proteins 680 and the replicated new viral genomes 620 are assembled 690 to new SARS-CoV-2 virus particles 692, which are thereafter released from the cell by exocytosis 691, as illustrated in phases 193, 294, 392.

The inventive medicinal component inhibiting the SARS-CoV-2 protein maturation within the host cell typically contains any of the following: weak bases, like ammonium salt, ammonium chloride, ammonium bicarbonate and chloroquine, vacuolar ATPase inhibitors, like bafilomycins and diphyllin, or ion channel modulators, like ivermectin in any combination or permutation.

The released viruses 692 can infect new cells and start the infection cycle again if the viral proteins are maturated, but with the inhibiting effect of the inventive medicine, this should not happen.

Interfering with the protein synthesis is likely to have greater side effects for patients than preventing the passage through the cell membrane of respiratory cells. Therefore, in some preferable embodiments the dose of the SARS-CoV-2 protein maturation inhibiting component 670 is kept lower, whereas dosage of the cell membrane passage inhibiting component 460, 580 is kept higher.

This might change the other way, if a new third extracellular SARS-CoV-2 pathway is discovered. Then it might be preferable to keep the dose of the SARS-CoV-2 protein maturation inhibiting component 670 higher, whereas dosage of the cell membrane passage inhibiting component 460, 580 is kept lower, or at sufficient level to block the two endosomal and non-endosomal pathways of embodiments 10 and 20.

Embodiment 60 can be readily combined with embodiments 10, 20, 30, 40, 50, 70, 80 and/or 90, because the intracellular and extracellular pathways described therein are in use simultaneously in a mammalian respiratory cell, in accordance with the invention.

Figure 7:
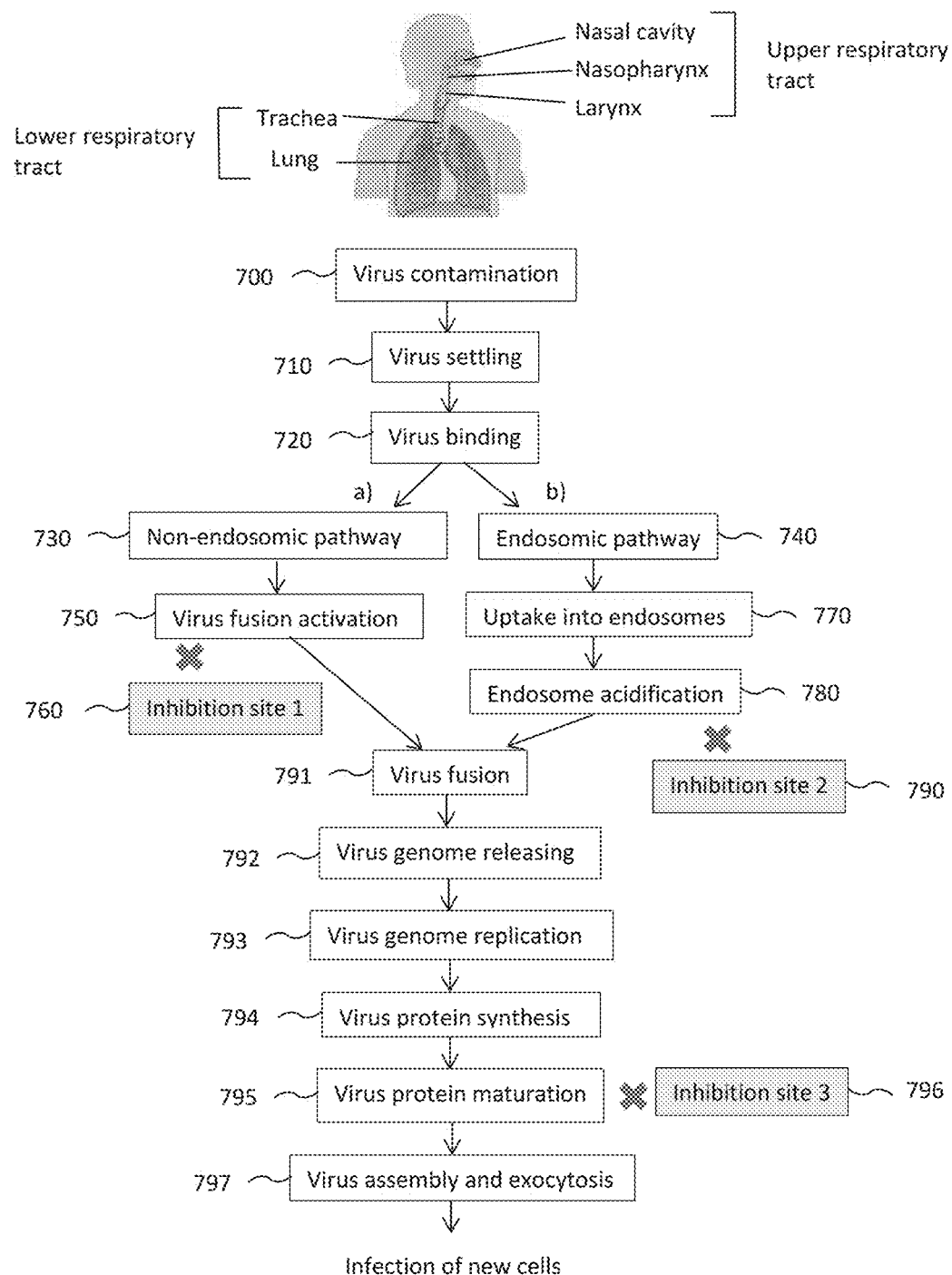
FIG. 7 shows the anatomical structure of human respiratory tract. It also describes the non-endosomic, endosomic, and intracellular viral pathways together to provide a functional presentation on how these pathways and the respective inventive medicinal impact on these pathways operate simultaneously in a mammalian cell as a flow diagram in embodiment 70 (inhibition sites 1, 2 and 3, phases 760, 790 and 796, respectively).

This FIG. 7 is a comprehensive presentation of SARS-CoV-2 virus entry pathways to the cell from its binding to its release out of the cell as an embodiment 70, and shows the impact sites (inhibition sites 1, 2 and 3) of the inventive medicine for inhibiting the propagation of the SARS-CoV-2 virus into the cell and within the cell.

In phase 700 the enveloped viruses, like SARS-CoV-2 coronavirus, enter and contaminate the respiratory tract either via direct contact of fingers or other virus carrying surfaces or via inhaled air. Virus can enter nasopharyngeal area through nose, mouth or eyes having a direct contact to nasal cavity. From upper airways, it can emanate downwards in the respiratory tract, and in more severe cases into lungs causing pneumonia. In some cases, it can go even to stomach causing e.g. diarrhea.

In phase 710 after contamination 700 SARS-CoV-2 virus approaches and settles down on respiratory tract mucosa. To initiate infection virus has to enter into the epithelial cells of the respiratory mucosa.

In phase 720 after settling 710 on the cell membrane, SARS-CoV-2 virus binds to a specific receptor on the surface of the respiratory tract epithelial cells. Each enveloped SARS-CoV-2 virus has its own specific receptor for binding. For SARS-CoV-2 this receptor is ACE2 membrane protein. In the case of SARS-CoV-2, this binding happens through virus surface S protein (spike) and cell membrane ACE2 receptor interaction.

After SARS-CoV-2 virus binding 720 to cell membrane receptor, two pathways 730 and 740 are initiated: a) non-endosomic pathway 730 (endocytosis independent pathway) and b) endosomic pathway 740 (endocytosis dependent pathway).

In phase 750 in non-endosomic pathway (a) 730 membrane protease, e.g. transmembrane protease serine subfamily 2 (TMPRSS2), activates ACE2 receptor and virus S protein for fusion 791 in pH independent manner. This activation is inhibited by the inventive medicine at inhibition site 1 760 by protease inhibitors, which may include e.g. camostat and/or aprotinin or another protease inhibitor.

In phase 770 in endosomic pathway (b) 740 after SARS-CoV-2 virus has bound to ACE2 on cell membrane, ACE2/virus complex is transferred into an early endosome through a clathrin-mediated endocytosis.

In phase 780 within the cytoplasm, the early endosome is acidified and matures to late endosome. This acidification can be inhibited at inhibition site 2 790 by the inventive medicine. The inventive medicine may include: weak bases, like ammonium salt, ammonium chloride, ammonium bicarbonate and chloroquine, vacuolar ATPase inhibitors, like bafilomycins and diphyllin, and/or ion channel modulators, like ivermectin in any combination or permutation in accordance with the invention.

In phase 791 SARS-CoV-2 Virus nucleocapsid fuses to cell membranes by the aid of proteases. They activate a fusion peptide part of the virus S protein, which then fuses the virus envelope into the cell membrane. This activation happens either in pH independent way 170 to cell membrane or in pH dependent way 280 to endosomal membrane.

In phase 792 after fusion 791, SARS-CoV-2 virus nucleocapsids that survived the inhibiting effects of the medicine in phases 760 and 790 enter into cell cytoplasm and dissemble, whereby the non-inhibited SARS-CoV-2 virus genetic material is released. In the case of SARS-CoV-2 coronaviruses, the genetic material is a single-stranded RNA genome.

In phase 793 after genome releasing 792 of SARS-CoV-2 virus genome, it replicates by reverse transcriptase enzyme produced by host cell's protein synthesis machinery.

In phase 794 the viral proteins and RNA genome (in the case of SARS-CoV-2) are synthesized using host cell's own protein synthesis machinery. At this point virus 'kidnaps' for its use the whole protein producing capacity of the cell and most of the products synthesized are viral (proteins, RNA).

After viral protein synthesis 794 the viral proteins, synthesized from the non-inhibited SARS-CoV-2 virus kidnapping of the protein synthesis machinery, are maturated in host cell's endoplasmic reticulum/Golgi compartment, e.g. by glycosylation. Some of these protein maturation reactions in Golgi apparatus are pH dependent (acidic). This maturation can be inhibited by the inventive medicine at inhibition site 3 796. The inventive medicine typically comprises weak bases, like ammonium bicarbonate and chloroquine. Also, vacuolar ATPase inhibitors, like bafilomycins and diphyllin, or ion channel modulators, like ivermectin, can be used in providing an inhibiting effect on viral protein maturation by the inventive medicine in this step.

In phase 797 after viral protein maturation 795, they and new genomic RNA molecules 793 are assembled in the cytoplasm to new infectious virus particles, if the dose of the inventive medicine in 796 is insufficient. In preferable embodiments the SARS-CoV-2 viral protein maturation is suppressed as much as possible within the constraints of the side effects that can be persevered by the patients in a short period. This period is typically a bit longer than the period of suspected exposure to SARS-CoV-2. After assembly, the SARS-CoV-2 virus particles would be released from the cell by exocytosis and can initiate the infection cycle in new cells.

Embodiment 70 can be readily combined with embodiments 10, 20, 30, 40, 50, 60, 80 and/or 90, because the intracellular and extracellular pathways described therein are in use simultaneously in a mammalian respiratory cell, in accordance with the invention.

Figure 8:
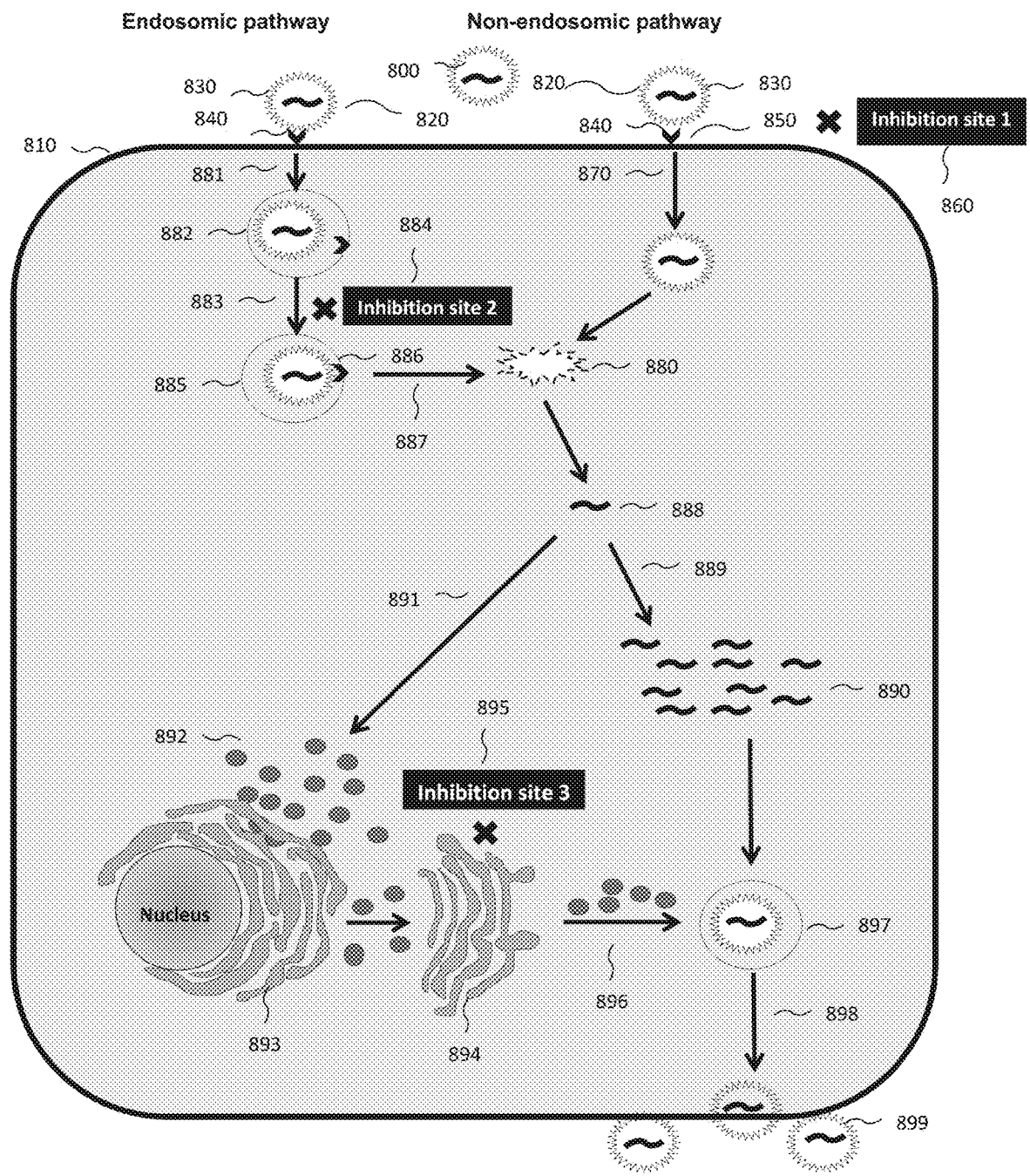
FIG. 8 describes the non-endosomic, endosomic, and intracellular viral pathways together to provide an anatomic presentation on how these pathways and the respective inventive medicinal impact on these pathways operate simultaneously in a mammalian cell as an embodiment 80 (inhibition sites 1, 2 and 3, phases 860, 884 and 895, respectively).

This FIG. 8 is a comprehensive presentation of virus entry pathways to the cell from its binding to its release out of the cell as an embodiment 80, and shows the impact sites (inhibition sites 1, 2 and 3) of the inventive medicine for inhibiting the propagation of the virus into the cell and within the cell.

After SARS-CoV-2 virus 800 has contaminated patient subject's respiratory tract, it approaches the cell membrane 810 as illustrated in phases 100, 200, 300, settles and binds 820 on cell surface to cellular receptor as illustrated in phases 110, 120, 210, 220, 310, 320, 420. In the case of SARS-Cov-2 virus, this happens through the interaction of virus S protein 830 and cellular receptor ACE2 840. After binding, two known pathways, a non-endosomic or endosomic entry, can initiate as illustrated in phases 130, 140, 230, 240, 330, 340, 730, 740. There might also be a third pathway for SARS-CoV-2 that we do not know yet.

In non-endosomic pathway, as illustrated in phases 130, 330, proteases activate in pH independent manner the S protein fusion peptide, which directs the SARS-CoV-2 virus envelope to fuse 850 into cell membrane 810, as illustrated in phases 150, 170, 350, 450. This fusion activation can be prevented by the inventive medicine at inhibition site 1 860 with proteinase inhibitors, as illustrated in phases 160, 460. After fusion, the virus 800 enters 870 into cellular cytoplasm and dissembles 880, releasing virus genome 888 (in the case of SARS-CoV-2 the genome is single stranded RNA), as illustrated in phases 180, 360, 480.

In endosomic pathway, as illustrated in phases 240, 340, after binding the virus 800 enters into cell by clathrin-mediated endocytosis 881, where the virus together with ACE2 receptor is uptaken into early endosome 882, as illustrated in phases 250, 350, 550. This early endosome later acidifies 883 by the function of lysosomes to late endosome 885, as illustrated in phases 260, 350, 570. This acidification can be inhibited by the inventive medicine at inhibition site 2 884 with weak bases, proton pump inhibitors and ion channel inhibitors, as illustrated in phases 270, 580. After acidification proteinases, like cathepsin, activate virus S protein 830 fusion peptide, which through interaction with ACE2 receptor 840 fuses 886 to endosomal membrane. After fusion, SARS-CoV-2 virus 800 enters 887 into cellular cytoplasm and dissembles 880, releasing virus genome 888 (in the case of SARS-CoV-2 the genome is single stranded RNA), as illustrated in phases 290, 360, 584.

The released SARS-CoV-2 virus genome 888 is then replicated 889 to new SARS-CoV-2 viral genomes 890 by cell's own machinery, as illustrated in phases 190, 291, 370, 482, 586. At the same time, the revealed SARS-CoV-2 virus genome 888 also initiates the synthesis 891 of viral proteins 892 by cell's own protein synthesis machinery, as illustrated in phases 191, 292, 380, 484, 588.

These proteins are synthesized in endoplasmic reticulum 893 and are transported into Golgi apparatus 894, where they mature to final proteins 896 at partly acidic conditions, as illustrated in phases 192, 293, 390, 487, 591. This maturation step can be inhibited by the inventive medicine at inhibition site 3 895 with weak bases, proton pump inhibitors and ion channel inhibitors, as illustrated in phases 391, 670. After Golgi apparatus 894, the mature viral proteins 896 and the replicated new viral genomes 890 are assembled 897 to new virus particles 899, which are thereafter released from the cell by exocytosis 898, as illustrated in phases 193, 294, 392, 490, 594, 691. These released viruses 899 can then infect new cells and start the infection cycle again.

There are thus at least three identified locations (inhibition sites 1, 2 and 3) in the viral pathways of enveloped SARS-CoV-2 viruses that can be targeted by the inventive drug molecules. Inhibition site 1 is indicated in embodiment 10, phase 160; embodiment 40, phase 460; embodiment 70, phase 760; embodiment 80, phase 860. Inhibition site 2 is indicated in embodiment 20, phase 270; embodiment 50, phase 580; embodiment 70, phase 790; embodiment 80, phase 884. Inhibition site 3 is indicated in embodiment 30, phase 391; embodiment 60, phase 670; embodiment 70, phase 796; embodiment 80, phase 895.

The function of inhibition site 1 160, 460, 760, 860, can be targeted by protease inhibitors in the inventive medicine, for instance camostat and aprotinin.

The function of inhibition site 2 270, 580, 790, 884 can also be targeted by inhibitors of vesicular acidification in the same inventive medicine, which may include any of the following: weak bases like ammonium salt, ammonium chloride, ammonium bicarbonate and chloroquine, inhibitors of vacuolar ATPase, like bafilomycins, diphyllin, and/or modulators of ion channels, like ivermectin.

The function of inhibition site 3 391, 670, 796, 895 can also be targeted by inhibitors of vesicular acidification in the same inventive medicine, which may include any of the following: weak bases like ammonium salt, ammonium chloride, ammonium bicarbonate and/or chloroquine, inhibitors of vacuolar ATPase like bafilomycins, diphyllin, and/or modulators of ion channels, like ivermectin.

The corresponding locations, where the inventive medicine acts, anatomically within the host cell are believed to be the following:

Inhibition site 1: Fusion of virus to the plasma membrane, as illustrated in phases 170, 350, 450, 750, 850, can be inhibited by protease inhibitors, e.g. TMPRSS2 inhibitors (e.g. camostat and aprotinin).

Inhibition site 2: Inhibition of endosomal acidification, as illustrated in phases 260, 570, 780, 883, will prevent cathepsin activation and thus inhibit fusion of viral envelope to the endosomal membrane preventing release of viruses into the cytoplasm for replication of viral RNA. Acidification can be inhibited by weak bases (like chloroquine, ammonium), proton pump inhibitors (like bafilomycins), and chloride channel inhibitors (like ivermectin).

Inhibition site 3: When viral SARS-CoV-2 RNAs enter the endoplasmic reticulum, they are translated to viral SARS-CoV-2 proteins. These proteins are then transported into the Golgi compartment, where they are maturated, as illustrated in phases 192, 293, 390, 795, 487, 591, 660, 894, e.g. by glycosylation. Some of the reactions are pH dependent and can be inhibited by either weak bases (like ammonium, ammonium salt, ammonium chloride, ammonium bicarbonate and chloroquine), proton pump inhibitors (like bafilomycins), or chloride channel modulators (like ivermectin).

The inventive medicine uses these aforementioned compounds in any permutation or combination in local administration by any of the following: nasal drops, nasal sprays or aerosols targeted into lower respiratory pathway) either alone or in the following combinations. The inventive medicine prevents the viral infection and/or to treats the infection in its early phase by decreasing viral entry into epithelial cells by any of the following exemplary compositions:

1. Ammonium alone
2. Chloroquine alone
3. Ivermectin alone
4. Camostat alone
5. Aprotinin alone
6. Vacuolar proton pump inhibitors alone (bafilomycins)
7. or any of these in combinations of two or more drugs, for instance chloroquine and camostat, chloroquine and camostat and ivermectin, etc.

Embodiment 80 can be readily combined with embodiments 10, 20, 30, 40, 50, 60 70, and/or 90 because the intracellular and extracellular pathways described therein are in use simultaneously in a mammalian respiratory cell, in accordance with the invention.

Nicotine is also known to be a weak base, pH 8.5. It has been shown in earlier in vitro studies that it could inhibit receptor mediated endosytosis. Due to the fact that it is a weak base it could penetrate cell membrane especially at pH near its isoelectric point and thus it may also effect glycosylation at Golgi compartment.

Very recent epidemiological studies from China (Farsalinos et al Systematic review of the prevalence of current smoking among hospitalized COVID-19 patients in China: could nicotine be a therapeutic option? Intern Emerg Med, May 10, 2020) have indicated that there are less smokers than expected among those men who get Covid 19 infection. This could be due to the inhibitory effect of nicotine on endosytosis and/or Golgi compartment.

The inventive medicine contains nicotine in some embodiments. Nicotine could inhibit entrance of enveloped viruses using receptor mediated endocytosis into the epithelial and other cells. We claim that using any kind of local or systemic administration of nicotine, to the respiratory or alimentary tract epithelium one can prevent or decrease entrance of SARS-CoV-2 into cells. Smoking could be one method of local administration, chewing of nicotine containing substances for instance nicotine tablets, and chewing tobacco or using of nicotine containing liquids or aerosols could also be used. Also nicotine administration through skin e.g. via nicotine containing gel, cream or plasters can be used. The effect of nicotine could be enhanced using a vehicle having neutral or slightly basic pH.

The invention has multiple advantages. Using local administration and especially more than one drug at the same time in the inventive medicine, it is possible to reduce the total dosage and decrease serious side effects known to be associated to each of above-mentioned drugs and still protect patients from COVID-19.

Method of administration of each compound and the inventive medicine could include any of the following exemplary drug delivery methods:
1. Nasal drops
2. Nasal or oral lavage
3. Nasal spray
4. Inhaled aerosol
5. Dosing of active substances through skin using gel or cream containing active substance or active substance containing plaster.
6. Chewing gum or gummy containing active substance or in case of nicotine also chewing tobacco.
7. Dosing of active substances through mouth epithelium via active substance containing tablets, snuff, white snuff, snuff pouch, other oral tobacco, and/or a nicotine pouch.
8. In addition, ammonium could be applied as gas in air inhaled by the patients.

One preferable recreational prophylactic for nicotine users/smokers, and possibly other people, could be the combination of ammonium and nicotine into an easily consumable oral pouch, which could be placed under the lip of the consumer for a few minutes.

In some exemplary embodiments of dosage of the inventive medicine, 1-10% of the maximal systemic dosage of each compound will be used.

Figure 9:
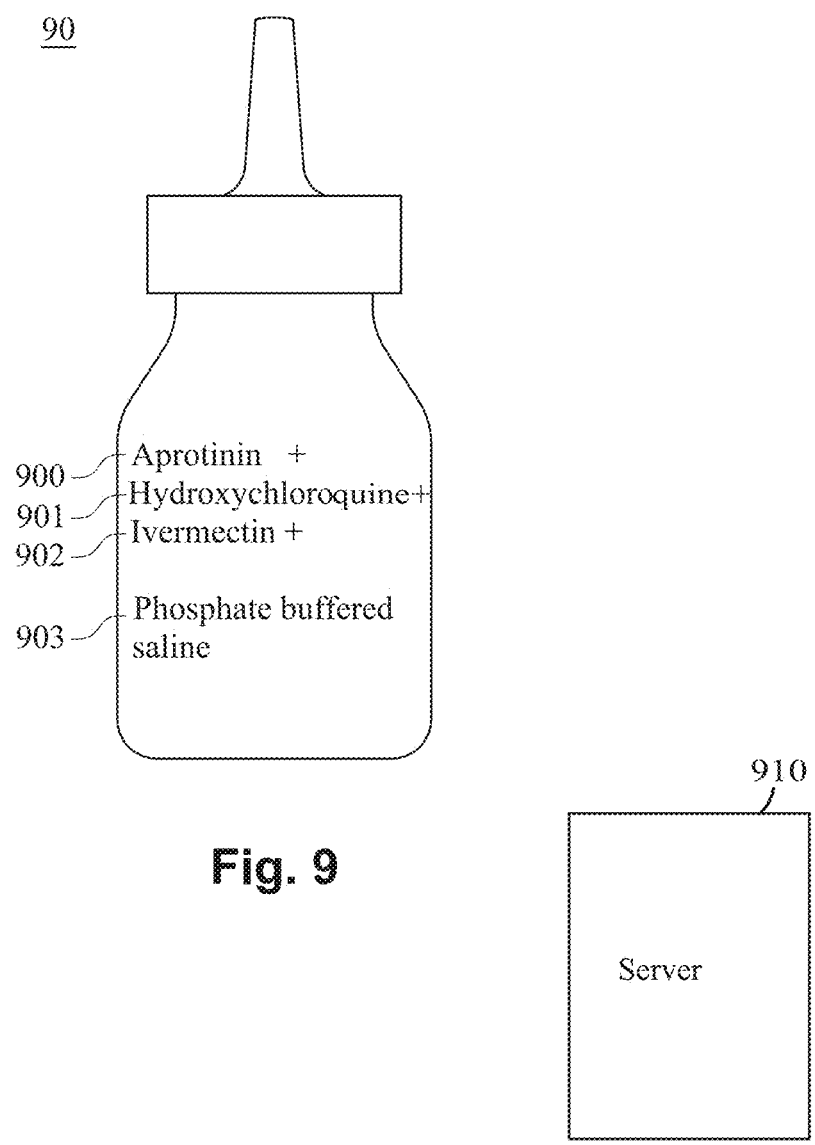
FIG. 9 describes an embodiment 90, an inventive nasal COVID-19 medicine realized in a portable bottle, which the user can carry e.g. in his pocket.

FIG. 9 shows an embodiment of a COVID-19 nasal spray in accordance with the invention. This nasal spray has been designed based on literature and past experience, but the inventors have not manufactured or produced this medicine at the time of filing. The inventive nasal spray is intended to be a prophylactic and very early phase treatment of COVID-19, or possibly even other related coated viruses that use receptor-mediated cell entry.

The principle of treatment is to attack the virus in the nasal mucosa and prevent its spread into the body. The treatment is preferably started as soon as possible or even before the actual infection, if the risk of infection is high. In some embodiments, the timing of treatment is preferably within a couple of hours after the suspected virus infection, and in any case before clinical symptoms appear. In patients who have developed clinical symptoms, the medicine is believed to not provide any benefit any longer. Therefore the inventive medicine should not be used at the symptom stage.

Preferably, length of the treatment is three days, if virus test after this 3-day treatment is negative. However, in the event of a quarantine period of for example, 2 weeks, depending on the quarantine policy in each country.

During the first days after viral exposure the dosing will preferably take place in 2-hour intervals 4-8 times daily. The route of administration is nasal. Nasal spray is the preferred device, which is typically injected/sprayed from the bottle 90 of FIG. 9 by pushing the tip of the bottle into the nostril of the patient, and spraying COVID-19 medicine into the nostril from the bottle 90.

The components and doses of the inventive nasal spray are:
Aprotinin 900 with a dose of 400-4000 Kallikrein Inhibitor Units (circa 56-560 micrograms)/day, and
Hydroxycholoroquine 901 with a dose of 0.4-4 mg/day, and
Ivermectin 902 with a dose of 0.01-0.1 mg/day.

In this application, the Kallikrein Inhibitor Units are understood as: "One Kallikrein Inhibitor Unit is identical to the quantity of protease inhibitor (e.g., aprotinin) that has the ability to inhibit two kallikrein units by 50% under optimal conditions. One Kallikrein Inhibitor Unit is equal to 0.025 antiplasmin units or 0.0031 trypsin inhibitor units. (NCI Thesaurus)."

In order to increase the solubility of ivermectin, one may use 2-5% (weight per volume, assuming g=mL) Tween 80, if necessary.

Volume of one spray injection from the bottle 90 is typically 0.1-0.3 mL. In some embodiments the daily volume used nasally is thus milliliters or fractions thereof. However, preferably the daily volume is minimized in some embodiments to increase the portability of the nasal spray by keeping the nasal spray bottle small.

The Aprotinin 900, Hydroxycholoroquine 901 and Ivermectin are typically dissolved into phosphate buffered saline 903. The phosphate buffered saline typically has a pH of 7.5-8.0 in accordance with the invention. Phosphate buffered saline is readily available as an "off the shelf" product from commercial providers such as Sigma-Aldrich. All compounds in FIG. 9 are water soluble and can be applied in concentrations, which have the intended therapeutic effect. Aprotinin is freely soluble in water (>10 mg/mL). Ivermectin can also be used as methanesulfonic acid salt (also called mesylate), which is soluble in water to 50 mg/mL. Hydroxychloroquine can be used as sulfate salt because it is highly water soluble, at least 200 mg/mL.

Typically, Aprotinin 900 is first dissolved into phosphate buffered saline on its own, in a separate container, in a higher concentration than its concentration is in the actual medicine. Similarly, Hydroxychloroquine 901 is first dissolved into phosphate buffered saline on its own in a separate container in a higher concentration than its concentration is in the actual medicine. Similarly, also Ivermectin 902 is first dissolved into phosphate buffered saline on its own in a separate container in a higher concentration than its concentration is in the actual medicine. Subsequently, the amounts of each individual solutions are calculated so that they in combination form a combined solution that provides the desired doses of each three (or more) medicine components with the dosing regimen, that is given or prescribed to the patient. Typically the inventive medicine of FIG. 9 is produced in room temperature and pressure, (RTP).

One preferable embodiment has mild but effective concentrations in the range of 0.1-5% of recommended daily dose. Inventors assume based on literature, that the daily dose of aprotinin is 100,000 KIU per adult. For Ivermectin the inventors assume that the daily dose is 600 micrograms/kg, so for an adult with weight 100 kg, i.e. 60000 micrograms, 60 mg. For Hydroxychloroquine inventors assume daily dose of 200 mg for adult.

The three or more pharmaceuticals would thus have the following percentages of systemic daily dose: aprotinin 4000 KIU/100,000 KIU=4%, ivermectin 100 micrograms/60000 micrograms=0.16%, Hydroxychloroquine 4 mg/200 mg=2%. These nasal doses could for example be packed into a daily spray volume of 0.4 mL. This would enable a nasal spray bottle of 10 mL size, with 25 daily doses in it. The calculated percentages are approximate, and do not take into account to volume increase caused by the introduction of the pharmaceutical into the fluid.

It is believed that the aforementioned pharmaceuticals would work despite some known side effects. Accumulation of chloroquine or hydroxychloroquine in the patient organs may result in deposits that can lead to blurred vision and blindness. Vomiting, headache and/or muscle weakness may also occur. Quinines have been associated with cases of retinal toxicity, particularly when provided at higher doses for longer times. With long-term doses, routine visits to an ophthalmologist are recommended. However, as the use is low dose and prophylactic it is believed that the side effects and the need for an ophthalmologist can be avoided.

Chloroquine and hydroxychloroquine are lysosomotropic agents, meaning they accumulate preferentially in the late endosomes and lysosomes of cells in the body. The pKa for the quinoline nitrogen of chloroquine is 8.5, meaning it is about 10% deprotonated at physiological pH (per the Henderson-Hasselbalch equation). Because the deprotonated form is more membrane-permeable than the protonated form, a quantitative "trapping" of the compound in lysosomes results with neutralization of vesicular pH.

Chloroquine has antiviral effects against some viruses, please see Savarino A, Boelaert J R, Cassone A, Majori G, Cauda R (November 2003). "*Effects of chloroquine on viral infections: an old drug against today's diseases?". The Lancet. Infectious Diseases.* 3 (11): 722-7. doi:10.1016/s1473-3099(03)00806-5. PMC 7128816. PMID 14592603. It increases late endosomal and lysosomal pH, resulting in impaired release of the virus from the endosome or lysosome—as the release of the virus requires a low pH. The virus is therefore unable to release its genetic material into the cell and replicate. Chloroquine also seems to act as a zinc ionophore that allows extracellular zinc to enter the cell and inhibit viral RNA-dependent RNA polymerase, please see:

Xue J, Moyer A, Peng B, Wu J, Hannafon B N, Ding W Q (1 Oct. 2014). "Chloroquine is a zinc ionophore". *PLOS ONE.* 9 (10):e109180. Bibcode:2014PLoSO . . . 9j9180X. doi:10.1371/journal.pone.0109180. PMC 4 182877. PMID 25271834, and te Velthuis A J, van den Worm S H, Sims A C, Baric R S, Snijder E J, van Hemert M J (November 2010). "Zn(2+) inhibits coronavirus and arterivirus RNA polymerase activity in vitro and zinc ionophores block the replication of these viruses in cell culture". *PLOS Pathogens.* 6 (11): e1001176. doi:10.1371/journal.ppat.1001176. PMC 2973827. PMID 21079686.

Ivermectin is a Food and Drug Administration (FDA)-approved antiparasitic drug that is used to treat several neglected tropical diseases, including onchocerciasis, helminthiases, and scabies. It is also being evaluated for its potential to reduce the rate of malaria transmission by killing mosquitoes that feed on treated humans and livestock. For these indications, ivermectin has been widely used and has demonstrated an excellent safety profile. Mode of action of ivermectin is to inhibit glutamate gated chloride channel. Inhibition of chloride channel will cause loss of pH gradient in respective cellular acidic compartments. Ivermectin is known to cause fever, itching or skin rash, joint or muscle pain when used systemically. With the topical nasal dosing and low amount of the compound side effects are expected to be few and mild.

Aprotinin, initially named "kallikrein inactivator", is a monomeric (single-chain) lobular polypeptide originally isolated from cow parotid glands in 1930. It has a molecular weight of 6512 and consists of 16 different amino acids. Aprotinin is the classic member of competitive inhibitors. Aprotinin has been studied in influenza patients after systemic and nasal administration and has shown some clinical activity. There are also several other serine proteases, more specifically trypsin, chymotrypsin and plasmin.

Host organisms must ensure that the activity of serine proteases is adequately regulated. This is achieved by a requirement for initial protease activation, and the secretion of natural inhibitors. Aprotinin has been studied in influenza patients both after systemic and nasal administration and has shown some clinical activity. Aprotinin as protein might not permeate into the nasal mucosal tissue. Aprotinin is known to raise the risk for kidney problems and coagulation disorders when given systemically. With the topical nasal dosing and low amount of the compound side effects are expected to be very few and mild.

Some proteases play a vital role in host cell-virus fusion activation by priming virus's Spike protein to show the protein named "fusion protein" (e.g. TMPRSS2 protease activate SARS-CoV-2 fusion). Recent study of Bojkova, Denisa; Bechtel, Marco; McLaughlin, Katie-May; McGreig, Jake E.; Klann, Kevin; Bellinghausen, Carla; Rohde, Gernot; Jonigk, Danny; Braubach, Peter; Ciesek, Sandra; Munch, Christian; Wass, Mark N.; Michaelis, Martin; Cinatl, Jindrich (2020). "Aprotinin Inhibits SARS-CoV-2 Replication". *Cells.* 9 (11): 2377. doi:10.3390/cells9112377. ISSN 2073-4409 suggests that aprotinin could inhibit SARS-CoV-2 replication. Therefore, the inventors believe that aprotinin has the desired clinical effect.

However, in some embodiments other protease inhibitors may be used to substitute aprotinin or complement aprotinin. Camostat mesylate is another protease inhibitor studied clinically. As a small molecule it may penetrate nasal mucosa and could inhibit the proteolytic activity also inside the cells. Camostat mesylate (Foipan™) is a particularly preferred form of camostat and is a known trypsin-like serine protease inhibitor that has been used to treat acute symptoms of chronic pancreatitis. Camostat mesylate and formulations thereof may be used in the treatment of diseases mediated by inhibition of a channel activating protease. Other potential protease inhibitor treatments for COVID-19 may include bromhexine, nafamostat, and benzquercin, which are considered to be used as inhibitor of TMPRSS2 at the clinical studies. Camostat and nafamostat are TMPRSS2 inhibitors currently approved to treat pancreatitis in Japan.

The above mentioned pharmaceuticals inhibit infection by blocking viral pathways via which the virus enters the cell, replicates, and/or synthesize proteins.

In some embodiments, embodiment 90 could also include a fourth pharmaceutical component aimed at the virus, namely the coat protein on the virus itself.

There are 13 disulfide bonds in the COVID-19 spike protein. Four of these disulfides are found in the outer surface of the spike receptor-binding domain that faces the outside part of the virus. These are known to be functionally important since antibodies against these regions of spike protein are neutralizing antibodies, please see: Ibrahim M. Ibrahima, Doaa H. Abdelmaleka, Mohammed E. Elshahata, Abdo A. Elfikyab. COVID-19 spike-host cell receptor GRP78 binding site prediction, (Journal of Infection Volume 80, Issue 5, May 2020, Pages 554-562).

Both the receptor-binding domain of the viral spike proteins and ACE2 have several cysteine residues. Molecular dynamics simulations studies revealed that the binding affinity was significantly impaired when all of the disulfide bonds of both ACE2 and SARS-CoV/CoV-2 spike proteins were reduced to thiol groups, please see, Hati S, Bhattacharyya S: Impact of Thiol-Disulfide Balance on the Binding of Covid-19 Spike Protein with Angiotensin-Converting Enzyme 2 Receptor ASC Publications, 2020, 5, 16292-16298.

These observations support the conclusion that targeting spike protein cysteines with reactive radical compound, like hypothiocyanite (OSCN⁻), will destroy at least part of the binding affinity of viral spike protein to it's receptor ACE-2. Thus, the combination of three (or more) cellular pathway affecting compounds, and one compound which is targeted to viral spike protein of the SARS-CoV/CoV-2 virus would further enhance the prophylactic effect of the inventive medicine.

The fourth compound in the nasal spray thiocyanate (SCN⁻) in some embodiments. In the body hypothiocyanite is formed by peroxidase catalysis of hydrogen peroxide and thiocyanate:

$$H_2O_2 + SCN^- \longrightarrow OSCN^- + H_2O.$$

The reaction product hypothiocyanite is a very reactive compound towards SH-groups. The action of OSCN⁻ against bacteria is known to be caused by sulfhydryl (SH) oxidation. OSCN⁻ has been identified as an antimicrobial agent in milk, saliva, tears, and mucus.

SCN⁻ is considered as a safe product as it is not mutagenic and is produced also by many mammalian cell types. Thiocyanate is also a stable product in conditions described below for nasal spray. Hypothiocyanite, however, is not stable enough in order to be suitable for a pharmaceutical product as such, but thiocyanate can be used as its prodrug in vivo. Thiocyanate can be added into the same bottle with the three or more of the above mentioned compounds targeting viral pathways. In addition, a very mild solution of $H_2O_2$ must be provided to the nasal mucosa by a second nasal spray bottle to activate thiocyanate to hypothiocyanite, which is the final active molecule towards sulphydryl groups of aminoacid cysteine of the viral spike protein.

In some embodiments, the nasal spray bottle has two separate containers, one for mild solution of $H_2O_2$, and another container for aprotinin 900, hydroxycholoroquine 901, ivermectin 903, and thiocyanate in a phosphate buffered saline 903. In some embodiments both containers may be sprayed from simultaneously or consecutively, activating the $H_2O_2$ and Thiocyanate on the nasal mucosa membrane, concurrently with the delivery of aprotinin 900, hydroxycholoroquine 901 and ivermectin 902 on the same nasal mucosa membrane.

In some embodiments the compositions of thiocyanate-based nasal spray could be Thiocyanate (0.5-5 mg/mL) and hydrogen peroxide ($H_2O_2$) 0.01-0.5 mg/mL. As an example the dosing schedule could be as follows: sodium thiocyanate and other pharmaceuticals are given together in one push as nasal spray. Daily dose of sodium thiocyanate can be 0.5-5 mg.

In some embodiments the $H_2O_2$ solution is given in a separate bottle 1) simultaneously with other drugs and 2) 2-3 times during the dosing intervals. Daily dose of $H_2O_2$ can be 0.1-5 mg.

For the spray bottle the compounds are dissolved in phosphate buffered isotonic saline.

Thiocyanate and $H_2O_2$ are both natural products and present in the human body practically in all tissues. Thiocyanate is known to be a safe compound. It has been used as blood pressure lowering drug with doses of several grams/day. At such very high doses both animal and human data support the role of thiocyanate in goitrogenesis. In the intended doses side effects are not expected. Physiologic thiocyanate concentrations in serum range from about 50 to 500 µmol/L (3-30 ug/ml) in humans depending on smoking status and food consumption. Higher concentrations are found e.g. in saliva.

Hydrogen peroxide is a reactive component, known to have significant antimicrobial properties. Its activity is regulated in the body by several peroxidase enzymes. It reacts rapidly and is a short-lived molecule in the biological material being thus potentially dangerous. In some embodiments dosing schedule can be different for safety reasons. For example, excess thiocyanate could preferably always be in the nasal mucosa and $H_2O_2$ should be administered in small doses more often than thiocyanate. It is expected that the dosing frequency is higher than that of thiocyanate and other viral pathway blocking pharmaceuticals.

Thiocyanate may be used as a sodium salt or a potassium salt (or any other water soluble, nontoxic and stable salt). Both salts are well (>100 mg/ml) water soluble. Hydrogen peroxide is a well known oxidant, sold e.g. for disinfection of wounds. It is available in pharmacies as aqueous solutions, with concentrations from <1% to 5%.

It is in accordance with the invention that the inventive nasal spray is used by patients in accordance with dosing instructions received via a mobile app, such as a iOS or Android, or Microsoft mobile App. By an app we mean a third party application, or an application, that is available to one or more commonly used mobile operating systems. In some embodiments the nasal spray bottle has electronic circuitry and is connected to the smartphone of the patient e.g. via a short range radio connection such as Bluetooth, NFC, IrDa or cable. In some embodiments the connection between the nasal spray bottle may be cellular data, such as 4G, 5G, and/or Wi-Fi or the like. In some embodiments the patient smartphone and the mobile application may operate the nasal spray bottle as a peripheral, for example an Apple Health or Google Health peripheral device.

In some embodiments the smartphone and the mobile application may control the nasal spray to provide a dose to the patient automatically, and/or alert the patient to take a prophylactic dose. For example, the mobile application may sound an alert or display a message indicating to the patient to take the dose from the nasal spray bottle.

Alternatively, the patient might be wearing "nostril pods" type of nasal peripheral device with prophylactic in it, in analogue to the famous AirPods popularized by Apple Computers. The smartphone and the mobile application will communicate to the nostril pod to spray a dose, for example via Bluetooth.

In one preferable embodiment mobile phone users, or health authorities indicate, via e.g. a mobile application or webpage, to a cloud service that the patient is infected, has been exposed to a potential virus infection, or that the patient has been vaccinated against the virus. The location of the mobile phone of this patient is then tracked. Eventually, as more and more people share their data to the cloud service, the cloud service will have very good awareness of time and location dependent risk of a user being exposed to a viral respiratory infection. If at the user location everyone in proximity is vaccinated, the risk is low. If there are no other people with exposed or infected status nearby, the risk is higher than with vaccinated people nearby, but still relatively low. If there are infected or exposed people nearby, there is some meaningful risk, and the mobile application may then instruct the user to inject a dose of nasal spray into his nostrils, or automatically activate the "nostril pods" to spray the dose into the nostrils of the user.

The aforementioned prophylactic cloud service is applicable against other viruses, and definitely against other viruses that infect via respiratory airways of a human. The three or more pharmaceuticals targeting cellular viral pathways are also likely to be effective against other viruses that have same or similar cellular entry mechanisms to SARS-CoV/CoV-2. The Thiocyanate and hydrogen peroxide ($H_2O_2$) is likely to be effective against other viruses that have similar spike proteins and/or viruses with disulfide bonds as in the COVID-19 spike protein. Especially if disulfides are found in the outer surface of the spike receptor-binding domain that faces the outside part of the virus, Thiocyanate and Hydrogen Peroxide ($H_2O_2$) is likely to be effective in mitigating viral binding to cells. The cleaving and breakage of the disulfide bonds typically not only creates a chemical change, but also the mechanical 3-dimensional structure of the spike protein is changed. Due to the mechanical change in the dimensions of the viral spike protein, this spike protein may also become mechanically unfit for cellular binding to mammalian respiratory cells.

Embodiment 90 can be readily combined with embodiments 10, 20, 30, 40, 50, 60, 70, and/or 80 because the intracellular and extracellular pathways described therein are in use simultaneously in a mammalian respiratory cell, in accordance with the invention.

Furthermore, it should be noted that bromhexine, gabexate and benzquercin may be used as protease inhibitors.

These are believed to inhibit viral fusion to the plasma membrane at inhibition site 1, as illustrated in phases 170, 350, 450, 750, 850. Please see, An Enzymatic TMPRSS2 Assay for Assessment of Clinical Candidates and Discovery of Inhibitors as Potential Treatment of COVID-19, *ACS Pharmacol. Transl. Sci.* 2020, 3, 5, 997-1007, Jonathan H Shrimp, Stephen C Kales, Philip E. Sanderson, Anton Simeonov, Min Shen, and Matthew D. Hall.

Furthermore, it should be noted that in principle inhibition of viral spike protein fusion to endosomal membrane can also be achieved by cathepsin L-inhibitors.

Furthermore, it should be noted that the inventive medicine prevents the viral infection and/or to treats the infection in its early phase by decreasing viral entry into epithelial cells by any of the following exemplary compositions:

1. Ammonium or ammonium salts alone
2. Hydroxychloroquine sulfate alone
3. Ivermectin mesylate alone
4. Camostat alone mesylate
5. Aprotinin alone
6. Vacuolar proton pump inhibitors alone (bafilomycins)
7. Cathepsin L inhibitors
8. or any of these in combinations of three or more drugs, for instance aprotinin, chloroquine and camostat, aprotinin chloroquine and camostat and ivermectin, etc.

It should be noted that the use of the nasal route for the delivery of challenging drugs such as small polar molecules, vaccines, hormones, peptides and proteins appears plausible. Due to the high permeability, high vasculature, low enzymatic environment of nasal cavity and avoidance of hepatic first pass metabolism, nasal route is well suitable for systemic delivery of drug molecules. Many drug delivery devices for nasal application of liquid, semisolid and solid formulation are well suitable for the delivery of biotechnological products in accordance with the invention. In nasal administration some allergic reactions and irritation of the mucosa are possible, although their incidence is probable low and severity is mild.

The invention has multiple advantages. Virus enters the body via inhalation through nasal mucosa. The invention discloses the method and pharmaceutical for building a 3-layered chemical shield or chemical mask to nasal mucosa. The battlefield of the virus and the human body is the nasal mucosa. The shield prevents the entry of viruses into the body just there. The inventive COVID-19 nasal pharmaceutical uses three mechanisms which are all necessary and important: 1) prevention of entry into the cell, 2) prevention of release of virus from endosomes 3) disturbing the building of virus particles by inhibiting glycosylation of viral proteins and prevention of virus exocytosis. For example, hydroxychloroquine is also known to inhibit viral exocytosis out from the cell. If we assume that each pharmaceutical reduces the virus transmission in it's aforementioned pathway (1, 2, 3) above, the aggregate virus transmission of the entire cell will be reduced in geometric progression, i.e. 0.5*0.5*0.5=0.125=to 12.5%, and of course further still if viral binding by spike protein is initially inhibited by reducing disulfide bonds. Thus, a mild dose with an arithmetic inhibiting effect on a singular viral pathway has the possibility to compound a very large inhibiting effect when a relevant mild dose is provided to inhibit multiple viral pathways. The inhibiting effect is further enhanced if the virus itself and its spike protein is targeted, e.g. if Thiocyanate and Hydrogen Peroxide ($H_2O_2$) diminish binding by 50%, the virus transmission will be reduced to 0.5*0.125%=0.0625%.

The three or more aforementioned drugs which are used in the inventive pharmaceutical have no antiviral activity. Instead, they modify cellular mechanisms. Thus, although COVID-19 is used as an example, the invention is not virus-specific and can be used against many viruses without spike proteins or disulfide bonds, which cause upper respiratory tract infections.

The inventive chemical shield is at its best in prevention, or in very early stage of infection. It should be given if the estimated risk of infection is high. The length of one treatment period is short, but treatment can be repeated later, if the risk of infection increases or continues.

As the number of virus particles is reduced and kept low in the human body by the inventive treatment, subjects under treatment do not infect other persons. The invention is applicable to many viruses different or similar from COVID-19, as the invention targets the mechanisms of the mammalian body for defense such as viral cell entry, viral endosomic entry, viral RNA processing in the endoplasmic reticulum, and virus binding to mammalian cell, rather than the non-binding core of the virus itself.

The inventive medicine comprising one or more compounds can be used to treat various viruses such as respiratory tract viruses. Illustrative, but non-limiting, examples of respiratory tract viruses include influenza virus, respiratory syncytial virus, parainfluenza viruses, metapneumovirus, rhinovirus, coronaviruses (such as COVID-19), adenoviruses, and bocaviruses.

The invention can be effectively used in prevention and slowing epidemic or pandemic diseases in the future. If a new virus is found and threatens human populations, this invention can be used as immediate treatment, while there is no vaccine, or during e.g. vaccine development. The invention is preferably used for short periods of time (days/weeks) in a localized fashion (nasal) as the inhibition of endocytosis or exocytosis, or protein synthesis may have undesirable consequences if the inhibiting effect takes place throughout the entire body for long durations of time.

Embodiments of the present disclosure also relate to a kit. The kit can be used to treat a respiratory tract virus. The kit includes a mouthwash and a toothpaste. The mouthwash can include thiocyanate, a thiocyanate salt, hydrogen peroxide, or combinations thereof. The toothpaste can include thiocyanate, a thiocyanate salt, hydrogen peroxide, or combinations thereof. Hydrogen peroxide and thiocyanate are kept in different containers (toothpaste, mouthwash), and combine in the mouth of the user as toothpaste and mouthwash are used together. Hypothiocyanate thus forms in the mouth of the user as mouthwash and toothpaste react. The mouthwash and/or the toothpaste further comprise one or more compounds that:

(1) inhibit endosomal acidification (260) preventing cathepsin activation and thus inhibit fusion of viral envelope to the endosomal membrane preventing release of SARS-CoV-2 viruses into the cytoplasm and the consequent replication of SARS-CoV-2 virus RNA in the mammalian respiratory cell; and/or (2) inhibit the fusion of the SARS-CoV-2 virus through the plasma membrane (150) of a mammalian respiratory cell, such as protease inhibitors or other compounds described herein; and/or (3) target viral RNAs in the endoplasmic reticulum, where the viral RNAs are arranged to be translated to viral proteins, and the viral proteins are arranged to be transported into the Golgi compartment of the mammalian respiratory cell, where the viral proteins are arranged to be glycosylated; and/or (4) inhibit spike protein binding to a mammalian respiratory cell; and/or (5) inhibit any of the preceding reactions and/or arranged to inhibit proton pumps (390).

The compounds that can be included in the mouthwash and/or toothpaste are described herein, including nicotine, chloroquine, chloroquine phosphate, hydroxychloroquine phosphate, chloroquine sulphate, hydroxychloroquine sulphate, proton pump inhibitor, bafilomycin, chloride channel inhibitor, ivermectin, weak base, ammonium salt, ammonium chloride, ammonium bicarbonate, TMPRSS2 inhibitor, camostat, aprotinin, ammonium, ammonium bicarbonate, bafilomycin, or combinations thereof. Other suitable embodiments described herein can be combined with this embodiment related to a kit.

Embodiments of the present disclosure also relate to a method of treating a respiratory tract virus. The method includes administering a therapeutically effective amount of a composition or medicine. The composition and/or medicine includes one or more compounds that:

(1) inhibit endosomal acidification (260) preventing cathepsin activation and thus inhibit fusion of viral envelope to the endosomal membrane preventing release of SARS-CoV-2 viruses into the cytoplasm and the consequent replication of SARS-CoV-2 virus RNA in the mammalian respiratory cell; and/or (2) inhibit the fusion of the SARS-CoV-2 virus through the plasma membrane (150) of a mammalian respiratory cell, such as protease inhibitors or other compounds described herein; and/or (3) target viral RNAs in the endoplasmic reticulum, where the viral RNAs are arranged to be translated to viral proteins, and the viral proteins are arranged to be transported into the Golgi compartment of the mammalian respiratory cell, where the viral proteins are arranged to be glycosylated; and/or (4) inhibit spike protein binding to a mammalian respiratory cell; and/or (5) inhibit any of the preceding reactions and/or arranged to inhibit proton pumps (390).

The compounds that can be included in the composition or medicine are described herein, including nicotine, chloroquine, chloroquine phosphate, hydroxychloroquine phosphate, chloroquine sulphate, hydroxychloroquine sulphate, proton pump inhibitor, bafilomycin, chloride channel inhibitor, ivermectin, weak base, ammonium salt, ammonium chloride, ammonium bicarbonate, TMPRSS2 inhibitor, camostat, aprotinin, ammonium, ammonium bicarbonate, bafilomycin, or combinations thereof. Other suitable embodiments described herein can be combined with this method of treating a respiratory tract virus.

Embodiments of the present disclosure also relate to a non-transitory computer-readable medium storing instructions that, when executed on a processor, perform operations described herein. The operations can include tracking the location of subscribers, tracking the infection status of subscribers, tracking the vaccination status of subscribers, and tracking the viral infection exposure status of subscribers on at least one cloud server. The operations can further include controlling and/or directing the administration of a prophylactic nasal medicine by sending an alert to a user/subscriber, notifying the user/subscriber to take a dose of the prophylactic medicine, and/or by controlling a peripheral nasal spray container of the user/subscriber to spray a dose of the medicine in said container of the peripheral. The alert to take a dose or the instruction to spray a dose of the medicine can be configured to take place at a location and time when the infection risk is calculated by the cloud server system to exceed a threshold value and/or parameter at the said location and time.

The non-transitory computer readable medium can be one or more of readily available memory such as random access memory (RAM), read only memory (ROM), or any other suitable form of digital storage, local or remote, in a mobile station or a server. FIG. 9 shows a cloud server 910 with a memory medium, from which alerts and instructions to take a dose, or to spray the nasal spray, are sent to the mobile application of the user (not shown), or directly to the nasal spray bottle via a radio path. The memory contains instructions, that when executed by the processor of the server 910 or the electronic nasal spray bottle 90 can facilitate one or more operations described herein. The instructions in the memory are in the form of a program product such as a program that implements one or more operations of the present disclosure. The program code of the program product may conform to any one of a number of different programming languages. Illustrative computer-readable storage media include, but are not limited to: (i) non-writable storage media (e.g., read-only memory devices within a computer such as CD-ROM disks readable by a CD-ROM drive, flash memory, ROM chips, or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer-readable storage media, when carrying computer-readable instructions that direct the functions of the methods described herein, are examples of the present disclosure. In one example, the disclosure may be implemented as the program product stored on a computer-readable storage media (e.g., memory) for use with a computer system (not shown). The program(s) of the program product define functions of the disclosure, described herein. Other suitable embodiments described herein can be combined with this embodiment related to a non-transitory computer-readable medium. In one preferred embodiment the server sends instructions to an electronic nasal spray bottle, or a mobile application of the consumer. In another embodiment the nasal spray bottle 900 is realized as a spray bottle spraying the prophylactic into inhaled air. For example, if infected people are detected in a subway, spray bottles e.g. in the air ventilation channels of the subway could be used spray the air in the subway with the prophylactic, in an attempt to avoid a mass spreading event. The spray bottles could be controlled by the server 910 via a radio connection or cable in preferred embodiments.

Embodiments Listing

The present disclosure provides, among others, the following aspects, each of which can be considered as optionally including any alternate aspects:

Clause 1. A medicine for COVID-19, characterized in that, the medicine is a pH increase inducing agent, and said medicine is administered to a patient to inhibit endosomal acidification (260) preventing cathepsin activation and thus inhibit fusion of viral envelope to the endosomal membrane preventing release of SARS-CoV-2 viruses into the cytoplasm and the consequent replication of SARS-CoV-2 virus RNA in the mammalian respiratory cell.

Clause 2. The medicine of Clause 1, characterized in that, the medicine comprises any of the following: nicotine, chloroquine, chloroquine phosphate and/or hydroxychloroquine phosphate and/or chloroquine phosphate and/or chloroquine sulphate and/or hydroxychloroquine sulphate.

Clause 3. The medicine of Clause 1 or Clause 2, characterized in that, the medicine is used as a prophylactic.

Clause 4. The medicine of any one of Clauses 1-3, characterized in that, the medicine comprises any of the following: weak base, nicotine, ammonium salt, ammonium chloride, ammonium bicarbonate, proton pump inhibitor, bafilomycin, and/or chloride channel inhibitor, ivermectin.

Clause 5. A medicine for COVID-19, characterized in that, the medicine comprises at least one protease inhibitor arranged to inhibit the fusion of the SARS-CoV-2 virus through the plasma membrane (150) of a mammalian respiratory cell.

Clause 6. The medicine of Clause 5, characterized in that, the protease inhibitors can be any of the following: TMPRSS2 inhibitors, camostat and/or aprotinin.

Clause 7. A medicine for COVID-19, characterized in that,
the medicine is arranged to target viral RNAs in the endoplasmic reticulum, and
the viral RNAs are arranged to be translated to viral proteins, and the viral proteins are arranged to be transported into the Golgi compartment of the mammalian respiratory cell, where the viral proteins are arranged to be glycosylated, and
the medicine is arranged to inhibit any of the preceding reactions and/or arranged to inhibit proton pumps (390).

Clause 8. The medicine as claimed in Clause 7, characterized in that, the medicine comprises any of the following: weak bases, nicotine, ammonium, ammonium salt, ammonium chloride, ammonium bicarbonate, chloroquine, and/or proton pump inhibitor, bafilomycin.

Clause 9. A medicine for COVID-19, characterized in that,
the medicine is a pH increase inducing agent, and said medicine is administered to a patient to inhibit endosomal acidification (260) preventing cathepsin activation and thus inhibit fusion of viral envelope to the endosomal membrane preventing release of SARS-CoV-2 viruses into the cytoplasm and the consequent replication of SARS-CoV-2 virus RNA in the mammalian respiratory cell, and
the medicine comprises protease inhibitors arranged to inhibit the fusion of the SARS-CoV-2 virus through the plasma membrane (150) of a mammalian respiratory cell, and
the medicine is arranged to target viral RNAs in the endoplasmic reticulum, and the viral RNAs are arranged to be translated to viral proteins, and the viral proteins are arranged to be transported into the Golgi compartment of the mammalian respiratory cell, where the viral proteins are arranged to be glycosylated, and
the medicine is arranged to inhibit any of the preceding reactions and/or arranged to inhibit proton pumps (390).

Clause 10. The medicine of Clause 9, characterized in that, the medicine comprises any of the following: nicotine, chloroquine, chloroquine phosphate and/or hydroxychloroquine phosphate and/or chloroquine phosphate and/or chloroquine sulphate and/or hydroxychloroquine sulphate, proton pump inhibitor, bafilomycin, and/or chloride channel inhibitor, ivermectin, protease inhibitors, TMPRSS2 inhibitors, camostat and/or aprotinin, weak bases, ammonium salt, ammonium chloride, ammonium bicarbonate, ammonium, chloroquine.

Clause 11. The medicine of any one of Clauses 1-4, characterized in that the method of administration of each compound could be any of the following: nasal drops, nasal lavage, nasal spray, inhaled aerosol, and/or applied as gas in inhaled air.

Clause 12. The medicine of Clause 5 or Clause 6, characterized in that the method of administration of each compound could be any of the following: nasal drops, nasal lavage, nasal spray, inhaled aerosol, and/or applied as gas in inhaled air.

Clause 13. The medicine of Clause 7 or Clause 8, characterized in that the method of administration of each compound could be any of the following: nasal drops, nasal lavage, nasal spray, inhaled aerosol, and/or applied as gas in inhaled air.

Clause 14. The medicine of Clause 9 or Clause 10, characterized in that the method of administration of each compound could be any of the following: nasal drops, nasal lavage, nasal spray, inhaled aerosol, and/or applied as gas in inhaled air.

Clause 15. The medicine of any one of Clauses 1-4 or 11, characterized in that the medicine dosage is 1-10% of the maximal systemic dosage of each compound for a patient or 0.1-5% of the systemic dosage.

Clause 16. The medicine of any one of Clauses 5, 6, or 12, characterized in that the medicine dosage is 1-10% of the maximal systemic dosage of each compound for a patient or 0.1-5% of the systemic dosage.

Clause 17. The medicine of any one of Clauses 7, 8, or 13, characterized in that the medicine dosage is 1-10% of the maximal systemic dosage of each compound for a patient or 0.1-5% of the systemic dosage.

Clause 18. The medicine of any one of Clauses 9, 10, or 14, characterized in that the medicine dosage is 1-10% of the maximal systemic dosage of each compound for a patient or 0.1-5% of the systemic dosage.

Clause 19. The medicine of any one of Clauses 1-4, 11, or 15 characterized in that, the medicine is used as a prophylactic.

Clause 20. The medicine of any one of Clauses 5, 6, 12 or 16, characterized in that, the medicine is used as a prophylactic.

Clause 21. The medicine of any one of Clauses 7, 8, 13, or 17, characterized in that, the medicine is used as a prophylactic.

Clause 22. The medicine of any one of Clauses 9, 10, 14, or 18, characterized in that, the medicine is used as a prophylactic.

Clause 23. A prophylactic medicine, characterized in that, the medicine is a pH increase inducing agent, and said medicine is administered to a patient to inhibit endosomal acidification (260) preventing cathepsin activation and thus inhibit fusion of viral envelope to the endosomal membrane preventing release of viruses into the cytoplasm and the consequent replication of virus RNA in the mammalian respiratory cell, and the medicine comprises protease inhibitors arranged to inhibit the fusion of the virus through the plasma membrane (150) of a mammalian respiratory cell, and the medicine is arranged to target viral RNA processing in the endoplasmic reticulum, and the viral RNAs are arranged to be translated to viral proteins, and the viral proteins are arranged to be transported into the Golgi compartment of the mammalian respiratory cell, where the viral proteins are arranged to be glycosylated, and the medicine is arranged to inhibit any of the preceding reactions and/or arranged to inhibit proton pumps (390).

Clause 24. A medicine as claimed in any one of Clauses 1-23, characterized in that, the medicine comprises Thiocyanate and Hydrogen Peroxide ($H_2O_2$), the virus has disulfide bonds, and one or more of these disulfide bonds are reduced to thiol groups by Thiocyanate and Hydrogen Peroxide ($H_2O_2$) in the medicine.

Clause 25. An intranasal COVID-19 medicine, comprising the combination of: aprotinin; hydroxychloroquine phosphate or hydroxychloroquine sulfate; and ivermectin.

Clause 26. An intranasal COVID-19 medicine, comprising the combination of: aprotinin; hydroxychloroquine phosphate or hydroxychloroquine sulfate; and bafilomycin.

Clause 27. An intranasal COVID-19 medicine, comprising the combination of: aprotinin; hydroxychloroquine phosphate or hydroxychloroquine sulfate; ivermectin; and bafilomycin.

Clause 28. An intranasal COVID-19 medicine, comprising the combination of: aprotinin; ammonia ammonium salt; and one or more of ivermectin or bafilomycin, or a combination thereof.

Clause 29. A medicine of any one of Clauses 22-28, characterized in that nicotine is added to the medicine.

Clause 30. A medicine as claimed in one or more of Clauses 1-29 characterized in that, the medicine comprises Thiocyanate and Hydrogen Peroxide ($H_2O_2$), the virus has disulfide bonds, and one or more of these disulfide bonds are cleaved, and thus the three dimensional structure of the spike protein in the virus is changed by the Thiocyanate and Hydrogen Peroxide ($H_2O_2$) in the medicine.

Clause 31. A computer program product, stored in a non-transient memory medium, configured to track the location, the infection status, vaccination status, and viral infection exposure status of subscribers on at least one cloud server, and control and/or direct the administration of prophylactic nasal medicine by sending an alert to a user, notifying the user to take a dose of the prophylactic medicine of any one of Clauses 1-30 and/or by controlling a peripheral nasal spray container of the user to spray a dose of the medicine of any one of Clauses 1-30 in said container of the peripheral, the alert to take a dose or the control instruction to spray a dose at the peripheral is configured to take place at a location and time when the infection risk is calculated by the cloud server system to exceed a threshold value and/or parameter at the said location and time.

Clause 32. A prophylactic or therapeutic for a respiratory tract disease administered within a respiratory tract of a mammal, comprising:
  a composition, the composition comprising:
    a first compound that inhibits spike protein binding to a mammalian respiratory cell;
    a second compound that inhibits virus penetration to a plasma membrane of the mammalian respiratory cell;
    a third compound that inhibits endosomal virus passage into a cell membrane of the mammalian respiratory cell; and
    a fourth compound that inhibits protein glycosylation based on viral RNA within the mammalian respiratory cell, wherein the first compound, the second compound, the third compound, and the fourth compound are the same or different.

Clause 33. The prophylactic or therapeutic of Clause 30, wherein:
  the first compound is selected from the group consisting of hydrogen peroxide, thiocyanate, thiocyanate salt, or combinations thereof;

the second compound is selected from the group consisting of a TMPRSS2 inhibitor, camostat, aprotinin, bromhexine, gabexate, benzquercin, and combinations thereof;

the third compound is selected from the group consisting of a weak base, an ammonium salt, ammonium chloride, ammonium bicarbonate, chloroquine, a proton pump inhibitor, bafilomycin, ivermectin, and combinations thereof; and the fourth compound is selected from the group consisting of chloroquine, chloroquine phosphate, hydroxychloroquine phosphate, chloroquine sulphate, hydroxychloroquine sulphate, proton pump inhibitor, bafilomycin, chloride channel inhibitor, ivermectin, weak base, an ammonium salt, ammonium chloride, ammonium bicarbonate, and combinations thereof.

Clause 34. The prophylactic or therapeutic of Clause 32 or Clause 33, wherein:

the first compound is selected from the group consisting of hydrogen peroxide, thiocyanate, thiocyanate salt, or combinations thereof;

the second compound is selected from the group consisting of camostat, aprotinin, bromhexine, gabexate, benzquercin, and combinations thereof;

the third compound is selected from the group consisting of ammonium chloride, ammonium bicarbonate, chloroquine, bafilomycin, ivermectin, and combinations thereof; and the fourth compound is selected from the group consisting of chloroquine, chloroquine phosphate, hydroxychloroquine phosphate, chloroquine sulphate, hydroxychloroquine sulphate, bafilomycin, ivermectin, ammonium chloride, ammonium bicarbonate, and combinations thereof.

Clause 35. The prophylactic or therapeutic of any one of Clauses 32-34, wherein the prophylactic or therapeutic is a prophylactic for respiratory tract virus.

Clause 36. The prophylactic or therapeutic of any one of Clauses 32-35, wherein the composition further comprises nicotine.

Clause 37. The prophylactic or therapeutic of any one of Clauses 32-36, wherein the second compound is selected from the group consisting of bromhexine, gabexate, benzquercin, or a combination thereof.

Clause 38. The prophylactic or therapeutic of any one of Clauses 32-37, wherein the prophylactic or therapeutic is a nasal dosage form, tooth paste, mouthwash, or any other dosage directed to be administered on internal epithelial walls of the respiratory tract of the mammal, or teeth, but not a digestive tract of the mammal.

Clause 39. The prophylactic or therapeutic of any one of Clauses 32-37, wherein the prophylactic or therapeutic is a nasal drop, a nasal lavage, a nasal spray, an inhaled aerosol, a gas, or combinations thereof.

Clause 40. The prophylactic or therapeutic of any one of Clauses 32-39, wherein an amount or dosage of each compound of the composition is 1-10% of a maximal systemic dosage for each compound administered to a patient.

Clause 41. The prophylactic or therapeutic of any one of Clauses 32-40, wherein an amount of each compound of the composition is 0.1-5% of a systemic dosage for each compound administered to a patient.

Clause 42. The prophylactic or therapeutic of any one of Clauses 32-41, wherein the prophylactic or therapeutic is an oral dosage form.

Clause 43. A kit, comprising:

a first composition comprising hydrogen peroxide; and a second composition comprising thiocyanate or a thiocyanate salt, wherein the first composition, the second composition, or both comprises one or more compounds, the one or more compounds comprising chloroquine, a chloroquine salt, hydroxychloroquine, a hydroxychloroquine salt, proton pump inhibitor, bafilomycin, chloride channel inhibitor, ivermectin, an ammonium salt, TMPRSS2 inhibitor, camostat, aprotinin, bafilomycin, or combinations thereof.

Clause 44. The kit of Clause 43, wherein the one or more compounds comprises chloroquine, chloroquine phosphate, hydroxychloroquine phosphate, chloroquine sulphate, hydroxychloroquine sulphate, bafilomycin, ivermectin, ammonium chloride, ammonium bicarbonate, camostat, aprotinin, or combinations thereof.

Clause 45. The kit of Clause 43 or Clause 44, wherein the first composition, the second composition, or both further comprises nicotine.

Clause 46. The kit of any one of Clauses 43-45, wherein the first composition, the second composition, or both further comprises bromhexine, gabexate, benzquercin, or combinations thereof.

Clause 47. The kit of any one of Clauses 43-46, wherein the first composition, the second composition, or both are formulated for nasal administration or directed to be administered on internal epithelial walls of a respiratory tract of a mammal, or teeth, but not a digestive tract of the mammal.

Clause 48. The kit of any one of Clauses 43-47, wherein the first composition, the second composition, or both, are in the form of a nasal spray, nasal drop, a nasal lavage, a nasal spray, an inhaled aerosol, a gas, or combinations thereof.

Clause 49. The kit of any one of Clauses 43-48, wherein the first composition, the second composition, or both are in are formulated for oral administration.

Clause 50. The kit of any one of Clauses 43-49, wherein the first composition and the second composition are administered prophylactically.

Clause 51. The kit of any one of Clauses 43-50, wherein: a daily dose of hydrogen peroxide in the first composition is from 0.01 mg to 5 mg; or a daily dose of thiocyanate in the second composition is 0.5 mg to about 5 mg; or a combination thereof.

Clause 52. The kit of any one of Clauses 43-51, wherein the one or more compounds of the second composition comprises aprotinin, hydroxychloroquine, a hydroxychloroquine salt, ivermectin, or combinations thereof.

Clause 53. The kit of any one of Clauses 43-52, wherein:

an amount or dosage of the one or more compounds is 1-10% of a maximal systemic dosage of each of the one or more compounds; or an amount or dosage of the one or more compounds is 0.1-5% of a systemic dosage of each of the one or more compounds; or a combination thereof.

Clause 54. A kit, comprising:

a mouthwash, the mouthwash comprising hydrogen peroxide; and a toothpaste, the toothpaste comprising thiocyanate or a thiocyanate salt, wherein the mouthwash, the toothpaste or both comprises one or more compounds, the one or more compounds comprising chloroquine, a chloroquine salt, hydroxychloroquine, a hydroxychloroquine salt, proton pump inhibitor, bafilomycin, chloride channel inhibitor, ivermectin, an ammonium salt, TMPRSS2 inhibitor, camostat, aprotinin, bafilomycin, or combinations thereof.

Clause 55. The kit of Clause 54, wherein the one or more compounds comprises chloroquine, chloroquine phosphate, hydroxychloroquine phosphate, chloroquine sulphate, hydroxychloroquine sulphate, bafilomycin, ivermectin, ammonium chloride, ammonium bicarbonate, camostat, aprotinin, or combinations thereof.

Clause 56. The kit of Clause 54 or Clause 55, wherein the mouthwash, the toothpaste, or both further comprises nicotine, bromhexine, or a combination thereof.

Clause 57. The kit of any one of Clauses 54-56, wherein the mouthwash, the toothpaste, or both further comprises gabexate, benzquercin, or combinations thereof.

Clause 58. The kit of any one of Clauses 54-57, wherein the mouthwash and toothpaste are used prophylactically.

Clause 59. The kit of any one of Clauses 54-58, wherein:
a daily dose of hydrogen peroxide in the mouthwash is from 0.01 mg to 5 mg; or
a daily dose of thiocyanate in the toothpaste is 0.5 mg to about 5 mg; or
a combination thereof.

Clause 60. The kit of any one of Clauses 54-59, wherein:
an amount or dosage of the one or more compounds is 1-10% of a maximal systemic dosage of each of the one or more compounds; or
an amount or dosage of the one or more compounds is 0.1-5% of a systemic dosage of each of the one or more compounds; or
a combination thereof.

Clause 61. A non-transitory computer-readable medium storing instructions that, when executed on a processor, perform operations, the operations comprising:
tracking a location of a subscriber, an infection status of the subscriber, a vaccination status of the subscriber, and a viral infection exposure status of the subscriber on at least one cloud server;
calculating an infection risk based on one or more of the location of the subscriber, the infection status of the subscriber, the vaccination status of the subscriber, or the viral infection exposure status of the subscriber; and
either:
sending an alert to the subscriber to take a dose of a prophylactic or a therapeutic when an infection risk is calculated to exceed a threshold value and/or parameter, or
controlling a peripheral nasal spray container to administer a dose of a prophylactic or a therapeutic from the peripheral nasal spray container to the subscriber when an infection risk is calculated to exceed a threshold value and/or parameter,
wherein the prophylactic or therapeutic comprises one or more compounds, the one or more compounds comprising chloroquine, a chloroquine salt, hydroxychloroquine, a hydroxychloroquine salt, proton pump inhibitor, bafilomycin, chloride channel inhibitor, ivermectin, an ammonium salt, TMPRSS2 inhibitor, camostat, aprotinin, bafilomycin, or combinations thereof.

The inventive medicine has been explained with reference to the earlier embodiments. However, the invention is not limited to these medicines and therapeutic uses but comprises all medicines within the spirit and scope of the inventive idea, and the claims that follow.

REFERENCES

1. Millet, J. K., Whittaker, G. R., 2018. Physiological and molecular triggers for SARS-CoV membrane fusion and entry into host cells. Virology 517, 3-8.
2. Zumla, A., Chan, J. F. W., Azhar, E. I., Hui, D. S. C., Yuen, K-Y., 2016. Coronaviruses-drug discovery and therapeutic options. Nat. Rev. Drug Discov. 15, 327-347.
3. US20140311482 A1, RHINOSINUSITIS PREVENTION AND THERAPY WITH PROINFLAMMATORY CYTOKINE INHIBITORS, published Oct. 23, 2014, Levitt, J. R.
4. Farsalinos et al. Systematic review of the prevalence of current smoking among hospitalized COVID-19 patients in China: could nicotine be a therapeutic option? Intern Emerg. Med., May 10, 2020.
5. Konstantinos Farsalinos Editorial: Nicotine and SARS-CoV-2:COVID-19 may be a disease of the nicotinic cholinergic system, Toxicology Reports 884, May 2020.
6. Ibrahim M. Ibrahima, Doaa H. Abdelmaleka, Mohammed E. Elshahata, Abdo A. Elfikyab. COVID-19 spike-host cell receptor GRP78 binding site prediction, (Journal of Infection Volume 80, Issue 5, May 2020, Pages 554-562).
Hati S, Bhattacharyya S: Impact of Thiol-Disulfide Balance on the Binding of Covid-19 Spike Protein with Angiotensin-Converting Enzyme 2 Receptor ASC Publications, 2020, 5, 16292-16298.
8. Bojkova, Denisa; Bechtel, Marco; McLaughlin, Katie-May; McGreig, Jake E.; Klann, Kevin; Bellinghausen, Carla; Rohde, Gernot; Jonigk, Danny; Braubach, Peter; Ciesek, Sandra; Münch, Christian; Wass, Mark N.; Michaelis, Martin; Cinatl, Jindrich (2020). "Aprotinin Inhibits SARS-CoV-2 Replication". *Cells*. 9 (11): 2377. doi:10.3390/cells9112377. ISSN 2073-4409.
9. Savarino A, Boelaert J R, Cassone A, Majori G, Cauda R (November 2003). "*Effects of chloroquine on viral infections: an old drug against today's diseases?*". The Lancet. Infectious Diseases. 3 (11): 722-7. doi:10.1016/s14733099(03)008065. PMC 7128816. PMID 14592603.
10. Xue J, Moyer A, Peng B, Wu J, Hannafon B N, Ding W Q (1 Oct. 2014). "Chloroquine is a zinc ionophore". *PLOS ONE*. 9 (10): e109180. Bibcode:2014PLoSO . . . 9j9180X. doi:10.1371/journal.pone.0109180. PMC 418287 7. PMID 25271834.
11. to Velthuis A J, van den Worm S H, Sims A C, Baric R S, Snijder E J, van Hemert M J (November 2010). "Zn(2+) inhibits coronavirus and arterivirus RNA polymerase activity in vitro and zinc ionophores block the replication of these viruses in cell culture". *PLOS Pathogens*. 6 (11): e1001176. doi:10.1371/journal.ppat.1001176. PMC 2973827. PMID 21079686.
12. An Enzymatic TMPRSS2 Assay for Assessment of Clinical Candidates and Discovery of Inhibitors as Potential Treatment of COVID-19, *ACS Pharmacol. Transl. Sci.* 2020, 3, 5, 997-1007, Jonathan H Shrimp, Stephen C Kales, Philip E. Sanderson, Anton Simeonov, Min Shen, and Matthew D. Hall.

What is claimed is:
1. A kit, comprising:
a mouthwash, the mouthwash comprising hydrogen peroxide; and
a toothpaste, the toothpaste comprising thiocyanate or a thiocyanate salt,
wherein the mouthwash, the toothpaste or both comprises one or more compounds, the one or more compounds comprising chloroquine, a chloroquine salt, hydroxychloroquine, a hydroxychloroquine salt, proton pump inhibitor, bafilomycin, chloride channel inhibitor, ivermectin, an ammonium salt, TMPRSS2 inhibitor, camostat, aprotinin, bafilomycin, or combinations thereof.
2. The kit of claim 1, wherein the one or more compounds comprises chloroquine, chloroquine phosphate, hydroxychloroquine phosphate, chloroquine sulphate, hydroxychlo- roquine sulphate, bafilomycin, ivermectin, ammonium chloride, ammonium bicarbonate, camostat, aprotinin, or combinations thereof.

3. The kit of claim 1, wherein the mouthwash, the toothpaste, or both further comprises nicotine, bromhexine, or a combination thereof.

4. The kit of claim 1, wherein the mouthwash, the toothpaste, or both further comprises gabexate, benzquercin, or combinations thereof.

5. The kit of claim 1, wherein the mouthwash and toothpaste are used prophylactically.

6. The kit of claim 1, wherein:
   a daily dose of hydrogen peroxide in the mouthwash is from 0.01 mg to 5 mg; or
   a daily dose of thiocyanate in the toothpaste is 0.5 mg to about 5 mg; or
   a combination thereof.

7. The kit of claim 1, wherein:
   an amount or dosage of the one or more compounds is 1-10% of a maximal systemic dosage of each of the one or more compounds; or
   an amount or dosage of the one or more compounds is 0.1-5% of a systemic dosage of each of the one or more compounds; or
   a combination thereof.

\* \* \* \* \*